US008795962B2

(12) United States Patent
Abu Khabar

(10) Patent No.: US 8,795,962 B2
(45) Date of Patent: Aug. 5, 2014

(54) EXPRESSION VECTORS BASED ON MODIFIED RIBOSOMAL PROTEIN PROMOTERS AND USES THEREOF IN POST-TRANSCRIPTIONAL ASSESSMENT

(75) Inventor: Khalid S. Abu Khabar, Riyadh (SA)

(73) Assignee: King Faisal Specialist Hospital and Research Center, Riyadh (SA)

( * ) Notice: Subject to any disclaimer, the term of this patent is extended or adjusted under 35 U.S.C. 154(b) by 195 days.

(21) Appl. No.: 13/000,556

(22) PCT Filed: Nov. 17, 2008

(86) PCT No.: PCT/EP2008/009712
§ 371 (c)(1),
(2), (4) Date: Mar. 30, 2011

(87) PCT Pub. No.: WO2009/155961
PCT Pub. Date: Dec. 30, 2009

(65) Prior Publication Data
US 2011/0312543 A1    Dec. 22, 2011

(30) Foreign Application Priority Data

Jun. 27, 2008  (WO) ................ PCT/EP2008/005278

(51) Int. Cl.
*C12Q 1/68* (2006.01)
*C12N 5/02* (2006.01)
*C12N 15/00* (2006.01)

(52) U.S. Cl.
USPC .......... 435/6.1; 435/6.13; 435/6.18; 435/440; 435/325

(58) Field of Classification Search
CPC .... C12N 15/85; C12N 15/8216; C12N 15/64; C12N 15/1079; C12N 15/63; C12Q 2545/114
See application file for complete search history.

(56) References Cited

U.S. PATENT DOCUMENTS 6,177,611 B1    1/2001  Rice
2008/0097088 A1*  4/2008  Simpson et al. ............. 536/24.1

FOREIGN PATENT DOCUMENTS

| WO | WO 01/21834 | 3/2001 |
| WO | WO 2004/013288 | 2/2004 |
| WO | WO 2005/000888 | 1/2005 |
| WO | WO 2005/095615 | 10/2005 |
| WO | WO 2006/081831 | 8/2006 |
| WO | WO 2006/123097 | 11/2006 |

OTHER PUBLICATIONS

Ysla et al, Assays of adenylate uridylate-rich element-mediated mRNA decay in cells; Methods in Enzymology, vol. 449, pp. 47-71, 2008.*
Arif et al., "A functional genomic analysis of calcium homeostasis in *Escherichia coli*", Abstracts of the General Meeting of the American Society for Microbiology, 101$^{st}$ General Meeting of the American Society for Microbiology, Orlando, Fl., May 20-24, 2001, abstract.
Castanotto et al., "Functional siRNA expression from transfected PCR products," *RNA*, Jan. 2002, vol. 8, No. 11, pp. 1454-1460.
Han et al., "Endotoxin-responsive sequences control cachectin/tumor necrosis factor biosynthesis at the translational level", *Journal of Experimental Medicine*, Feb. 1, 1990, vol. 171, No. 2, pp. 465-475.
He et al., "Interference of porcine reproductive and respiratory syndrome virus replication on MARC-145 cells using DNA-based short interfering RNAs," *Antiviral Research*, May 2007, vol. 74, No. 2, pp. 83-91.
Lu et al., "Gene expression enhancement mediated by the 5' UTR intron of the rice *rubi3* gene varied remarkably among tissues in transgenic rice plants", *Molecular Genetics and Genomics*, Jun. 2008, vol. 279, No. 6, pp. 563-572.
Moor et al. "Mechanisms of translational control by the 3' UTR in development and differentiation", *Seminars in Cell & Developmental Biology*, Feb. 2005, vol. 16, No. 1, pp. 49-58.
Roa-Rodríguez, "Promoters used to regulate gene expression," retrieved from the Internet: URL: http://www.patentlens.net/daisy/promoters/768.html>, published Apr. 11, 2007, 191 pages.
Sambrook et al., "Molecular Cloning", *Cold Spring Harbor Laboratory Press*, 2001, 3rd edition, pp. 8.37-8.45, 9.36-9.37, 17.30-17.51, XP-002497435.
Wilkie et al., "Regulation of mRNA translation by 5'- and 3'-UTR-binding factors", *TRENDS in Biochemical Sciences*, Apr. 2003, vol. 28, No. 4, pp. 182-188.
Yoshihama et al., "The human ribosomal protein genes: sequencing and comparative analysis of 73 genes", *Genome Research*, Mar. 2002, vol. 12, No. 3, pp. 379-390.

* cited by examiner

*Primary Examiner* — Celine Qian
*Assistant Examiner* — Addison D Ault
(74) *Attorney, Agent, or Firm* — Saliwanchik, Lloyd & Eisenschenk

(57) ABSTRACT

The present invention relates to expression vector comprising (a) a promoter region comprising a non-inducible constitutively active ribosomal protein gene promoter, (b) an operably linked reporter or gene sequence, and (c) a 3' untranslated region (3' UTR), which are suitable means for an selective assessment of post-transcriptional regulation, post-transcriptional control elements and factors as well as for identifying compounds that effect post-transcription. The present invention furthermore relates to arrays, expression vector libraries and cell lines containing the expression vector(s). The present invention furthermore relates to a method and kit for identifying compounds that affect post-transcriptional regulation of reporter(s) or gene(s), that utilize the expression vector(s).

19 Claims, 5 Drawing Sheets

SEQUENCE LISTING

```
<160> NUMBER OF SEQ ID NOS: 10

<210> SEQ ID NO 1
<211> LENGTH: 3504
<212> TYPE: DNA
<213> ORGANISM: Homo sapiens

<400> SEQUENCE: 1
agcgtggcct tgtttgtacc tccatgattg cctggctggc cttgctaacc taatcacatc      60
tgtgacggga tatagtgatg tttaatctta tgattgcctt aagaattaag gcaatcagac     120
gggttcggcg gctcatgcct gtaatcccag cactttggga ggccgaggcg ggcggatcac     180
gaggtcagaa gatccagtcc atcctggcta acaaggtgaa accccgtctc tactaaaaat     240
acaaaaaatt agccgggcat ggtggcggga gcctgtagtc ccagctactc gggaggctga     300
ggcaggagga tggcgtgaat ctgggaggcg gagcttgcag tgggccgaga tcgcgccact     360
gccctccagc ctgggcgaca gagcgagact ccgtctcaaa aaaaaaaaaa aaagaatta     420 aggcaatcat aattccccac gcacactcat atgctaggac cccgcccctt acctgaaacg     480
ttgtggctta tatagacact gccaggcact gtgttaagtg ctcccaaaga gcacccagt     540 ctaccatttt ccctctcgat tctatatgta cactcgggac aagttctcct gatcgaaaac     600
ggcaaaacta aggcccaag taggaatgcc ttagttttcg gggttaacaa tgattaacac     660
tgagcctcac acccacgcga tgccctcagc tcctcgctca gcgctctcac caacagccgt     720
agcccgcagc cccgctggac accggttctc catcccgca gcgtagcccg gaacatggta     780
gctgccatct ttacctgcta cgccagcctt ctgtgcgcgc aactgtctgg tcccgcccg     840 tcctgcgcga gctgcctgcc caggcaggtt cgccggtgcg agcgtaaagg ggcggagcta     900
ggactgcctt gggcggtaca aatagcaggg aaccgcgcgg tcgctcagca gtgacgtgac     960
acgcagccca cggtctgtac tgacgcgccc tcgttcttc ctctttctcg actccatctt    1020
cgcggtagct gggaccgccg ttcaggtaag aatgggcct tggctggatc cgaagggctt    1080
gtagcaggtt ggctgcgggg tcagaaggcg cgggggggaac cgaagaacgg ggcctgctcc    1140
```

```
gtggccctgc tccagtccct atccgaactc cttgggaggc ctggccttcc ccacgtgagc    1200
cgccgcgacc accatcccgt cgcgatcgtt tctggaccgc tttccactcc caaatctcct    1260
ttatcccaga gcatttcttg gcttctctta caagccgtct tttctttact cagtcgccaa    1320
tatgcagctc tttgtccgcg cccaggagct acacaccttc gaggtgaccg gccaggaaac    1380
ggtcgcccag atcaaggtaa ggctgcttgg tgcgccctgg gttccatttt cttgtgctct    1440
tcactctcgc ggcccgaggg aacgcttacg agccttatct ttccctgtag gctcatgtag    1500
cctcactgga gggcattgcc ccggaagatc aagtcgtgct cctggcaggc gcgcccctgg    1560
aggatgaggc cactctgggc cagtgcgggg tggaggccct gactaccctg gaagtagcag    1620
gccgcatgct tggaggtgag tgagagagga atgttctttg aagtaccggt aagcgtctag    1680
tgagtgtggg gtgcatagtc ctgacagctg agtgtcacac ctatggtaat agagtacttc    1740
tcactgtctt cagttcagag tgattcttcc tgtttacatc cctcatgttg aacacagacg    1800
tccatgggag actgagccag agtgtagttg tatttcagtc acatcacgag atcctagtct    1860
ggttatcagc ttccacacta aaattaggtc agaccagggc ccccaaagtg ctctataaaa    1920
ttagaagctg gaagatcctg aaatgaaact taagatttca aggtcaaata tctgcaactt    1980
tgttctcatt acctattggg cgcagcttct ctttaaaggc ttgaattgag aaaagagggg    2040
ttctgctggg tggcaccttc ttgctcttac ctgctggtgc cttcctttcc cactacaggt    2100
aaagtccatg gttccctggc ccgtgctgga aaagtgagag gtcagactcc taaggtgagt    2160
gagagtatta gtggtcatgg tgttaggact ttttttcctt tcacagctaa accaagtccc    2220
tgggctctta ctcggtttgc cttctccctc cctggagatg agcctgaggg aagggatgct    2280
aggtgtggaa gacaggaacc agggcctgat taaccttccc ttctccaggt ggccaaacag    2340
gagaagaaga agaagaagac aggtcgggct aagcggcgga tgcagtacaa ccggcgcttt    2400
gtcaacgttg tgcccacctt tggcaagaag aagggcccca atgccaactc ttaagtcttt    2460
tgtaattctg gctttctcta ataaaaagc cacttagttc agtcatcgca ttgtttcatc     2520
tttacttgca aggcctcagg gagaggtgtg cttctcgggt tggtggtatg tccctagga    2580 gaacagtgag gcagaaaagg cagaagcctt tggtatgggg ggaagaaatg gtaaactaca    2640
agagaaattt cctgtgaaga aacagctaca gatcctgggg ggcttcagat gtaaaattgg    2700
ggttattccc tatcctaagt aacttgatca gtcccccag tcattcttt ttcatcttct      2760 aaacagagaa ggtagcagga atcactgtgg tgagaggttt gttatggagg cagcaataga    2820
agggatgggt gggggaagag gtttgtatag aaggtgaacc tggccgttcc ctgaacttgg    2880
taccagctgt ggccttagag tccagggcag gaatctggtc tgccttggtt ttagaagtaa    2940
atattatgtt gggagcatgg cctcgtttgt acctctgtga ctgcctggcc ggacttggta    3000
acctaatcac atctgtgatt ggatatagtg aggtttcagt gttcccaaaa gttgggttac    3060
ctctggggct gattcagggt tctcttctgg caactgagcc tcccagcact ctgaaccccc    3120
acttactcat tcagctaaag tttctggacc tgccagttct tgagaaatag catccaacag    3180
ggtaaagccc ttgggctgtg gactttgact gcctgagttt ggaccttctt tttcttccta    3240
ctccatttac tgggtggctg cctttgaac taactactaa tttaatctct gccatctcca    3300
gggctgctgt gagggttaaa ggatgtaaat caacatctgg cttacagtga gtgtgtgaat    3360
cttggctatt tttgtctctg tggtgttaaa gacatggttc ctgccttcca gcagtttaga    3420 aaggggagg atgtggacag atacaatagc atcccagaga gggcctcttt ttttgttttt    3480
```

```
cttttttcttt tattttattt tatt                                         3504

<210> SEQ ID NO 2
<211> LENGTH: 4289
<212> TYPE: DNA
<213> ORGANISM: Homo sapiens

<400> SEQUENCE: 2
gtctggcaca tagaaggcat ttttaaacat ccttgctgag tgaaccaata tcccagaaac      60
ctctcacagc tagttcatct tacaggagaa acagtattaa agagttaatt aaatggccag     120
gcgcggtggc tcacgcctgt aatcccagca cattgggagg ccgaggcggg cggatcactc     180
gaggtcagga gatcgacacc agcctggcca acatggtgaa accccctctc tactgaaaat     240
acaaacatca gccaggcgtg atggtggaag cctgtaatcc cagctactca ggaggctgag     300
gtgggacaat cgcttgaacc cgggaggcgg aggttgtagt gagccaagat cgcaccactg     360
cacaacagcc tagaagacag agtgagaccc tgtctcagaa aaaataaaa ataaaaataa      420 ataaatctat aagtaaatga ctcgccagtc aaaataaacg gcaactttag ggttaaaggc     480
ccaatctggc tccaaagctt ggggttttag ttactacact acattgcttc actatatttt     540
acaatttact agctgcttat aagtatgaat taaggctcag aagtctaatt ttccagacta     600
ctcggaggac tctcgcccca ctccactcca caaagattca gctcagcgac tccttcctac     660
tctgacctag ccccgcgtcc cgctctcagt ggcttgggca agagcgcctg cgcggtgagc     720
gggtcccata aaacgcattc tgggattggt agtccatgtt cctccggtct ccagcattca     780
aaagaaaaag ggggaaaaaa aaccatgcaa attagatatc tctgaatttc ttgcaaatta     840
aataagacgc agattctggc tcaggaaagt gatgcaaacg cgtcgttttc aaaggagaga     900
ccccagcctc gggtcaggcg cggcgcagac agcggcgcgg ggtccttggc tgggcggggc     960
ttgctcgcgg tggcttgtgg ctccttcctg cggtgcttct ctctttcgct caggcccgtg    1020
gcgccgacag gatgggtgag ctgttgtggc cggtttaagg gcgctgcaag cgggacttgg    1080
ggtcttgggg acgggcgggc ggatgcgaat agagtagggc gggggatgcc atggagaggc    1140
tccatggggg agggccgggg aagcgccgct ccaggaggca cgtggtccgg cgcggaaggg    1200
gcccatgagg cgtggaggcc gccgaggtcg gggtaccgag ggacgcaggg aggccagcgc    1260
ttcctcccgg gcattcgagc ggggcctcgt ccttcgggag aacacattct ccggagccct    1320
cttcgaacgt ttattagtcg gttcagggca acttgaaggc caaatgtttg gcccacaggc    1380
caataaatag tacgagagcc aatcggctta agggtttatt ccaggtgagg cgagtgtctt    1440
agaagatggg aaacacgtag atggcgtgtt tttacggaag aactaaaata tttaattttt    1500
aggcaagtgt cgtggacttc gtactgctag gaagctccgt agtcaccgac gagaccagaa    1560
gtggcatgat aaacagtata agaaagctca tttgggcaca gccctaaagg ccaacccttt    1620
tggaggtgct tctcatgcaa aaggaatcgt gctggaaaaa gtgtaagtcc attgctcccg    1680
tcaagtttta gtttattata ggaattcgag acatgaactt acgaattctt gttttgaaag    1740
taattgcagg tttttgtgta gtagtattca tttgggcatt gtggggtaaa attgcaaagc    1800
gtttgttcta tttaaaagtt ggtaaaatta gttttttggga attaggtagt aaggttttta   1860
atttaacgtt ggcctggaag gaattggaga agatactagc aatgatgaag taaaggacac    1920 aaacacctttt actgtgggag ttgttataag taaatggcac gtgtcagcta ttgaacttta   1980
tcgacttgat aaaactaagg tgaagagaag tgacttgcat cagaattaat tgaggtcata    2040 caccctaagat tgagacatga aactgccagt atttgactgg ttttgacttt ttaaaataat   2100
```

```
aatttcatat agttctatca tatttgatgg tagagccatt ttaacccaga ctttttttt    2160
ttttttttt tttttgaga cagtctagct ctgtcaccca ggctggtgtg cagtagcgca     2220
agactccctg caaccttagc ctcccaggtt caagcatttc tcctgcctca gcctcccagg   2280
tagctgggat tacaggcgcc cactaccaca ccagctaata ttttgtattt tcagtagtga   2340
tggggtttca ccatgttgac caggctagtc tcaaactcct gacctcaggt gataatgcct   2400
gcttcggcct ccgaaagtgc tggaattaca ggcgtgagcc actgtgtccg cccagactt    2460
tctaattctt acctcagata cctttttttct ttttctttt ttttttttg agatagggtc    2520
ccttgtcaca caggctggcc atcttgacgt tctaggcata gatcctccca cgtcagcctc   2580
gcaagtagtt gggactacag gcccacgctg ccactccagt ctactttat aactgtaaaa    2640
ggtctagaaa ttttcccccat tgtgctaatg aaattaagac tggcagaaaa ctaggttgac   2700
atcacaggac ttcagctcag ccatttgagg ttagattgaa aagatagaaa cagtttctca   2760
ttagttctct agttaatatg aaaagataat cttttttcaga aagccagctc acagtgctgt  2820
gcctttttgta tttcagagga gttgaagcca aacagccaaa ttctgccatt aggaagtgtg  2880
taagggtcca gctgatcaag aatggcaaga aaatcacagc ctttgtaccc aatgacggtt   2940
gcttgaactt tattgaggtg agtatttcaa ctctatcgta ccttctgttc ttggggtggc   3000
ctccctcaca ttttatctg atgcaaggga gtttcctcac atgaaagtat ttttgtgatc    3060
gccaccaaca ccagaaataa acttcttatt ttattccagg aaaatgatga agttctggtt   3120
gctggatttg gtcgcaaagg tcatgctgtt ggtgatattc ctggagtccg ctttaaggtt   3180
gtcaaagtag ccaatgtttc tcttttggcc ctatacaaag gcaagaagga aagaccaaga   3240
tcataaatat taatggtgaa aacactgtag taataaattt tcatatgcca aaaaatgttt   3300
gtatcttact gtcccctgtt ctcaccacga agatcatgtt cattaccacc accacccccc   3360
cttattttt ttatcctaaa ccagcaaacg caggacctgt accaattta ggagacaata    3420
agacagggtt gtttcaggat tctctagagt taataacatt tgtaacctgg cacagtttcc   3480
ctcatcctgt ggaataagaa aatgggatag atctggaata aatgtgcagt attgtagtat   3540
tactttaaga actttaaggg aacttcaaaa actcactgaa attctagtga gatactttct   3600
ttttattct tggtattttc catatcgggt gcaacacttc agttaccaaa tttcattgca    3660
catagattat cttaggtacc cttggaaatg cacattcttg tatccatctt acaggggccc   3720
aagatgataa atagtaaaact caaaattgct ccccactctg tttattattt aaaggtgtca  3780
ggatctgtgt tgtaatgtgt ctacattaat gtgtttagga gaatacaggc attggatcat   3840
ttagttgatg aagtatatg ccaggcaagg gagataaggt atacgacaag actgatgttt    3900
tcagtatctt ctcatgaggt tgtcagagac cttcatgtct tcaaagacta gtcagcaaat   3960
gaagtggttt agtgtagaga caagattggt tgtgttttga taatttaagc taggtattga   4020
gtacatgtgg atttgctgt ccacaaatac ttgtttcaga gttttcatgg atacagtggc    4080
atggttgaaa tgaagctgtg agccttctgc tttaaatctg atgtaagaaa ctcctgttaa   4140
caaatagtaa gtatgggtta attagcccctt tgatcaaagc ctagctttac attgtttagg  4200
atctttggaa aacaattggt ttggttgccc actttccgta ggatcaagag cagaaccttt   4260
cacatggcac agaagaaccc aggttgcgc                                    4289
```

<210> SEQ ID NO 3
<211> LENGTH: 733
<212> TYPE: DNA

<213> ORGANISM: Artificial
<220> FEATURE:
<223> OTHER INFORMATION: modified RPS30 promoter region

<400> SEQUENCE: 3

```
gatatcggca aaactaaggc cccaagtagg aatgccttag ttttcggggt taacaatgat    60
taacactcct gagcctcaca cccacgcgat gccctcagct cctcgctcag cgctctcacc   120
aacagccgta gcccgcagcc ccgctggaca ccgggtctcc atccccgcag cgtagcccgg   180
aacatggtag ctgccatctt tacctgctac gccagccttc tgtgcgcgca actgtctggt   240
cccgccccgt cctgcgcgag ctgcctgccc aggcaggttc gccggtgcga gcgtaaaggg   300
gcggagctag gactgccttg ggcggtataa atagcaggga accgcgcggt cgctcagcag   360
tgacgtgaca cgcagcccac ggtctgtact gacgcgccct cgcttcttcc tctttctcga   420
ctccatcttc gcggtagctg ggaccgccgt tcaggtaaga atggggcctt ggctgcagcc   480
gaagggcttg tagcaggttg gctgcggggt cagaaggcgc gggggaacc gaagaacggg    540
gcctgctccg tggccctgct ccagtcccta tccgaactcc ttgggaggcc tggccttccc   600
cacgtgagcc gccgcgacca ccatcccgtc gcgatcgttt ctggaccgct ttccactccc   660
aaatctcctt tatcccagag catttcttgg cttctcttac aagccgtctt ttctttactc   720
agtcgccgtc gac                                                      733
```

<210> SEQ ID NO 4
<211> LENGTH: 781
<212> TYPE: DNA
<213> ORGANISM: Artificial
<220> FEATURE:
<223> OTHER INFORMATION: modified RPS30 promoter region

<400> SEQUENCE: 4

```
gatatctagc cgggcatggt ggcgggagcc tgtagtccca gctactcggg aggctgaggc    60
aggaggatgg cgtgaatctg ggaggcggag cttgcagtgg gccgagatcg cgccacttga   120
gcctcacacc cacgcgatgc cctcagctcc tcgctcagcg ctctcaccaa cagccgtagc   180
ccgcagcccc gctggacacc gggtctccat ccccgcagcg tagcccggaa catggtagct   240
gccatcttta cctgctacgc cagccttctg tgcgcgcaac tgtctggtcc cgccccgtcc   300
tgcgcgagct gcctgcccag gcaggttcgc cggtgcgagc gtaaaggggc ggagctagga   360
ctgccttggg cggtacaaat agcagggaac cgcgcggtcg ctcagcagtg acgtgacacg   420
cagcccacgg tctgtactga cgcgccctcg cttcttcctc tttctcgact ccatcttcgc   480
ggtagctggg accgccgttc aggtaagaat ggggccttgg ctgcagccga agggcttgta   540
gcaggttggc tgcggggtca gaaggcgcgg gggaaccga agaacggggc ctgctccgtg    600
gccctgctcc agtccctatc cgaactcctt gggaggcctg gccttcccca cgtgagccgc   660
cgcgaccacc atcccgtcgc gatcgtttct ggaccgcttt ccactcccaa atctcctta    720
tcccagagca tttcttggct tctcttacaa gccgtctttt ctttactcag tcgccgtcga   780
c                                                                   781
```

<210> SEQ ID NO 5
<211> LENGTH: 781
<212> TYPE: DNA
<213> ORGANISM: Artificial
<220> FEATURE:
<223> OTHER INFORMATION: modified RPS30 promoter region

<400> SEQUENCE: 5

```
gatatctagc cgggcatggt ggcgggagcc tgtagtccca gctactcggg aggctgaggc    60
aggaggatgg cgtgaatctg ggaggcggag cttgcagtgg gccgagatcg cgccacttga   120
gcctcacacc cacgcgatgc cctcagctcc tcgctcagcg ctctcaccaa cagccgtagc   180
ccgcagcccc gctggacacc gggtctccat ccccgcagcg tagcccggaa catggtagct   240
gccatcttta cctgctacgc cagccttctg tgcgcgcaac tgtctggtcc cgccccgtcc   300
tgcgcgagct gcctgcccag gcaggttcgc cggtgcgagc gtaaaggggc ggagctagga   360
ctgccttggg cggtataaat agcagggaac cgcgcggtcg ctcagcagtg acgtgacacg   420
cagcccacgt tctgtactga cgcgccctcg cttcttcctc tttctcgact ccatcttcgc   480
ggtagctggg accgccgttc aggtaagaat ggggccttgg ctgcagccga agggcttgta   540
gcaggttggc tgcggggtca gaaggcgcgg ggggaaccga agaacggggc ctgctccgtg   600
gccctgctcc agtccctatc cgaactcctt gggaggcctg gccttcccca cgtgagccgc   660
cgcgaccacc atcccgtcgc gatcgtttct ggaccgcttt ccactcccaa atctccttta   720
tcccagagca tttcttggct tctcttacaa gccgtctttt ctttactcag tcgccgtcga   780
c                                                                  781

<210> SEQ ID NO 6
<211> LENGTH: 992
<212> TYPE: DNA
<213> ORGANISM: Artificial
<220> FEATURE:
<223> OTHER INFORMATION: modified RPS23 promoter region

<400> SEQUENCE: 6
gatatctggc caggcgcggt ggctcacgcc tgtaatccca gcacattggg aggccgaggc    60
gggcggatca ctcccagact actcggagga ctctcgcccc actccactcc acaaagattc   120
agctcagcga ctccttccta ctctgaccta gccccgcgtc ccgctctcag tggcttgggc   180
aagagcgcct gcgcggtgag cgggtcccat aaaacgcatt ctgggattgg tagtccatgt   240
tcctccggtc tccagcattc aaaagaaaaa gggggaaaaa aaccatgca aattagaatc    300 tctgaatttc ttgcaaatta ataagacgc agattctggc tcaggaaagt gatgcaaacg    360
cgtcgttttc aaaggagaga ccccagcctc gggtcaggcg cggcgcagac agcggcgcgg   420
ggtccttggc tgggcgggc ttgctcgcgg tggcttgtgg ctccttcctg cggtgcttct    480
ctctttcgct caggcccgtg gcgccgacag gctgggtgag ctgttgtggc cggtttaagg   540
gcgctgcaag cgggacttgg ggtcttgggg acgggcgggc ggatgcgaat agagtagggc   600
gggggatgcc atggagaggc tccatggggg agggccgggg aagcgccgct ccaggaggca   660
cgtggtccgg cgcggaaggg gcccatgagg cgtggaggcc gccgaggtcg ggtaccgag    720 ggacgcaggg aggccagcgc ttcctcccgg gcattcgagc ggggcctcgt ccttcgggag   780
aacacattct ccggagccct cttcgaacgt ttattagtcg gttcagggca acttgaaggc   840
caaatgtttg gcccacaggc caataaatag tacgagagcc aatcggctaa gggtttattc   900
caggtgaggc gagtgtctta gaagatggga aacacgtaga tggcgtgttt ttacggaaga   960
actaaaatat ttaattttta ggcaaggtcg ac                                 992

<210> SEQ ID NO 7
<211> LENGTH: 793
<212> TYPE: DNA
<213> ORGANISM: Artificial
<220> FEATURE:
```

<223> OTHER INFORMATION: modified RPS30 promoter region

<400> SEQUENCE: 7

```
gatatcggca aaactaaggc cccaagtagg aatgccttag ttttcggggt taacaatgat    60
taacactcct gagcctcaca cccacgcgat gccctcagct cctcgctcag cgctctcacc   120
aacagccgta gcccgcagcc ccgctggaca ccgggtctcc atccccgcag cgtagcccgg   180
aacatggtag ctgccatctt tacctgctac gccagccttc tgtgcgcgca actgtctggt   240
cccgccccgt cctgcgcgag ctgcctgccc aggcaggttc gccggtgcga gcgtaaaggg   300
gcggagctag gactgccttg gcggtataaa atagcaggga catccctatc agtgatagac   360
catccctatc agtgatagac catccctatc agtgatagac accgcgcggt cgctcagcag   420
tgacgtgaca cgcagcccac ggtctgtact gacgcgccct cgcttcttcc tctttctcga   480
ctccatcttc gcggtagctg ggaccgccgt tcaggtaaga atggggcctt ggctgcagcc   540
gaagggcttg tagcaggttg gctgcggggt cagaaggcgc gggggggaacc gaagaacggg   600
gcctgctccg tggccctgct ccagtcccta tccgaactcc ttgggaggcc tggccttccc   660
cacgtgagcc gccgcgacca ccatcccgtc gcgatcgttt ctggaccgct ttccactccc   720
aaatctcctt tatcccagag catttcttgg cttctcttac aagccgtctt ttctttactc   780
agtcgccgtc gac                                                      793
```

<210> SEQ ID NO 8
<211> LENGTH: 793
<212> TYPE: DNA
<213> ORGANISM: Artificial
<220> FEATURE:
<223> OTHER INFORMATION: modified RPS30 promoter region

<400> SEQUENCE: 8

```
gatatcggca aaactaaggc cccaagtagg aatgccttag ttttcggggt taacaatgat    60
taacactcct gagcctcaca cccacgcgat gccctcagct cctcgctcag cgctctcacc   120
aacagccgta gcccgcagcc ccgctggaca ccgggtctcc atccccgcag cgtagcccgg   180
aacatggtag ctgccatctt tacctgctac gccagccttc tgtgcgcgca actgtctggt   240
cccgccccgt cctgcgcgag ctgcctgccc aggcaggttc gccggtgcga gcgtaaaggg   300
gcatccctat cagtgataga ccatccctat cagtgataga ccatccctat cagtgataga   360
ccggagctag gactgccttg gcggtataaa atagcaggga accgcgcggt cgctcagcag   420
tgacgtgaca cgcagcccac ggtctgtact gacgcgccct cgcttcttcc tctttctcga   480
ctccatcttc gcggtagctg ggaccgccgt tcaggtaaga atggggcctt ggctgcagcc   540
gaagggcttg tagcaggttg gctgcggggt cagaaggcgc gggggggaacc gaagaacggg   600
gcctgctccg tggccctgct ccagtcccta tccgaactcc ttgggaggcc tggccttccc   660
cacgtgagcc gccgcgacca ccatcccgtc gcgatcgttt ctggaccgct ttccactccc   720
aaatctcctt tatcccagag catttcttgg cttctcttac aagccgtctt ttctttactc   780
agtcgccgtc gac                                                      793
```

<210> SEQ ID NO 9
<211> LENGTH: 238
<212> TYPE: DNA
<213> ORGANISM: Homo sapiens

<400> SEQUENCE: 9

```
gatgttgtga ggacatgtgg aagcacttta agttttttca tcataacata aattatttc     60
```

```
aagtgtaact tattaaccta tttattattt atgtatttat ttaagcatca aatatttgtg      120
caagaatttg gaaaaataga agatgaatca ttgattgaat agttataaag atgttatagt      180
aaatttattt tattttagat attaaatgat gttttattag ataaatttca atcagggt       238

<210> SEQ ID NO 10
<211> LENGTH: 250
<212> TYPE: DNA
<213> ORGANISM: Homo sapiens

<400> SEQUENCE: 10
aagacctcac ctagaaattg acacaagtgg accttaggcc ttcctctctc cagatgtttc       60
cagacttcct tgagacacgg agcccagccc tccccatgga gccagctccc tctatttatg      120
tttgcacttg tgattattta ttatttattt attatttatt tatttacaga tgaatgtatt      180
tatttgggag accggggtat cctgggggac ccaatgtagg agctgccttg gctcagacat      240
gttttccgtg                                                             250
```

EXPRESSION VECTORS BASED ON MODIFIED RIBOSOMAL PROTEIN PROMOTERS AND USES THEREOF IN POST-TRANSCRIPTIONAL ASSESSMENT

CROSS REFERENCE TO A RELATED APPLICATION

This application is a National Stage Application of International Application Number PCT/EP2008/009712, filed Nov. 17, 2008; which claims priority to International Application PCT/EP2008/005278, filed Jun. 27, 2008; which are incorporated herein by reference in their entirety.

The present invention relates to expression vector comprising (a) a promoter region comprising a non-inducible constitutively active ribosomal protein gene promoter, (b) an operably linked reporter or gene sequence, and (c) a 3' untranslated region (3' UTR), which are suitable means for an selective assessment of post-transcriptional regulation, post-transcriptional control elements and factors as well as for identifying compounds that effect post-transcription. The present invention furthermore relates to arrays, expression vector libraries and cell lines containing the expression vector(s). The present invention furthermore relates to a method and kit for identifying compounds that affect post-transcriptional regulation of reporter(s) or gene(s), that utilize the expression vector(s).

BACKGROUND OF THE INVENTION

Transcriptional regulation occurs as a result of many different signaling pathways that lead to an activation of transcriptional factors that regulate promoter transcriptional activity. Alterations in gene expression leading to transcription and transcriptional regulation can be induced by a wide variety of inducers, stress, insults, environmental changes, and during development and other biological processes such as cellular growth, innate immunity, and metabolism. Reporter gene technology is a widely used and important approach to assess promoter activity or expression and changes in gene expression as a result of transcriptional regulation. The term "reporter" refers to a gene product that can be easily measured when it is fused to transcriptional control elements, such as those in promoters, and that "reports" the effect of a signalling cascade or experimental conditions on gene expression in living cells. The promoter is best known to be located immediately upstream of a transcription start site of a gene and often comprises a core promoter, is generally within 50 bp of the transcription site where the pre-initiation complex forms along with a general transcription machinery which assembles including polymerase II, and an extended promoter that can contain specific regulatory sequences elements (Cooper et al., 2006).

Regulated gene technologies including reporter gene technology is important both in academic basic scientific research and in pharmaceutical industry research. For example, it is used to monitor transcriptional activity of a specific promoter of interest or a cis-acting sequence of interest in health, disease, or therapeutic intervention research setting. The specific promoter of interest can be synthesized de novo or purposely altered, for example, by introducing specific mutations. Reporter gene technology is also used to assess the activity of transacting factors on specific promoters or sequences.

Regulated gene technologies including reporter gene technology is widely used in drug industry to discover and assess modulators, e.g., inhibitors, of the activity of specific promoters, specific cis-acing sequences, or of trans-acting factor activity. A drug discovery assay based on reporter gene technology is based on the measurement of transcription activity of a detectable reporter that is operably linked to promoters or specific cis-acting sequence elements that are activated by signaling cascades allowing a screening for compounds that modulate the transcriptional activity. The transcriptional reporter system can be studied for the effect of a new gene product or drug candidate on a particular signal transduction pathway.

Notable examples of cis-acting elements are, but not limited to, NFκB elements, AP-1 elements, IFN-stimulated response elements (ISRE), metal response elements, c-myc response elements, p53 response elements, calcium response elements, and many others. Intracellular receptors such as hormone receptors, e.g. glucocorticoid receptor, estrogen receptor, and androgen receptor, can also mediate transcription and can reach the nucleus either in its native state or modified by a specific signaling event.

Many of the regulatory transcriptional elements are used with reporter assays in a drug discovery program. For the purpose of providing an example, NFκB is one of these important elements in inflammation and cancer. This protein is a member of the rel family of transcription factors that regulate several important physiological processes, including immune responses, inflammation, cell growth, apoptosis, and tumorigenesis. As a result, the NF-κB signaling pathway has been increasingly seen as a promising target for pharmacological intervention, especially in models of inflammation or cancer, where the pathway is often constitutively active (Calzado et al., 2007). Many different stimuli have been identified which activate the NF-κB pathway such as the pro-inflammatory cytokines tumor necrosis factor (TNF-α) and interleukin-1 (IL-1). There are many signaling pathways that regulate transcription that can be targeted by drugs. These signaling events result in modification and activation of transcriptional factors that subsequently act on the transcriptional machinery. Thus, the transcription reporter assays are important in pharmaceutical industry.

However, when post-transcriptional assessment is desired instead of assessing transcriptional effects, different regulated gene technologies including reporter gene technology have to be utilized, namely systems without or with minimal interference of transcriptional effects.

Thus, there is a need in the art for improved means and methods in the field of regulated gene technologies.

Thus, the object of the present invention is to provide means and methods that allow studying (post-)transcriptional regulation, in particular an improved assessment of post-transcriptional effects.

SUMMARY OF THE INVENTION

The object of the present invention is solved by the subject-matter as defined in the attached claims.

In particular, the object of the present invention is solved by providing an expression vector.

An expression vector according to the present invention comprises
(a) a promoter region comprising a non-inducible constitutively active ribosomal protein gene promoter,
(b) an operably linked reporter or gene sequence, and
(c) a 3' untranslated region (3' UTR).

According to the present invention this object is furthermore solved by using the expression vectors according to the present invention for assessing post-transcriptional effects.

According to the present invention this object is furthermore solved by using the expression vectors according to the present invention for producing an array.

According to the present invention this object is furthermore solved by providing an array produced according to the present invention that comprises at least an expression reporter or gene construct of the present invention.

According to the present invention this object is furthermore solved by providing a library of expression vectors comprising at least 2 expression vectors according to the present invention, wherein each expression vector comprises a different post-transcriptional control element.

According to the present invention this object is furthermore solved by providing a stable cell line that harbors the expression vector according to the present invention, and preferably expresses a reporter or gene protein therefrom.

According to the present invention this object is furthermore solved by a method for identifying compounds that affect post-transcriptional regulation of reporter(s) or gene(s).

A method according to the present invention preferably comprises the following steps:
(1) providing
   at least one expression vector as defined herein,
   at least one linear expression cassette derived from the expression vector as defined herein,
   an array as defined herein,
   a library of expression vectors as defined herein, and/or
   a stable cell line as defined herein,
(2) providing at least a compound to be tested,
(3) determining the effect of the compound on the post-transcriptional regulation by determining the mRNA level and/or the expression level of the reporter or gene.

According to the present invention this object is furthermore solved by providing a kit for carrying out the method according to the present invention, comprising
(i) at least one expression vector as defined herein,
   and/or
   at least one linear expression cassette derived from the expression vector as defined herein,
(ii) a transfection reagent, and
(iii) an instruction sheet.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Expression Vectors Suitable for Assessing Post-Transcriptional Effects

As outlined above, the present invention provides expression vectors comprising
(a) a promoter region comprising a non-inducible constitutively active ribosomal protein gene promoter,
(b) an operably linked reporter or gene sequence, and
(c) a 3' untranslated region (3' UTR).

The expression vector is a nucleic acid construct.

The nucleic acid is preferably DNA, RNA, PNA or comprises modified nucleotides, nucleosides. The expression vector construct can comprise different types of nucleic acids.

Promoter Region (a)

The expression vector according to the present invention comprises a promoter region that comprises a non-inducible constitutively active ribosomal protein gene promoter.

The term "non-inducible constitutively active promoter" refers to a promoter that is constitutively active in a manner that is independent on transcriptional induction.

A non-inducible constitutively active promoter differs from a minimal promoter, because minimal promoters give very weak expression levels and it is difficult to achieve sensitivity and selectivity, in particular with the use of 3'UTR from labile cellular mRNAs, and they are furthermore particularly problematic with the use of drug inhibitors that further attenuate expression levels.

When normally used in regulated gene technology for assessing a transcriptional activation due to specific transacting factors, a promoter linked to specific gene/reporter products is usually minimal to reduce basal background levels and achieve higher transcriptional induction in order to facilitate end measurements. Several minimal promoters are known in the art such as those derived from promoters of the cytomegalovirus (CMV), HSV-1 TK, SV40; and they contain few transcriptional control elements in addition to an RNA polymerase II recognition TATA or TATA-like box. Minimal promoters can also include a CCAAT protein binding site and SP1 site. A minimal promoter includes a TATA box such as TATAAA or its variants. Promoters, either full or partial, can be used to assess transcriptional activation such as in the case of new genes.

However, studies requiring post-transcriptional assessment rely on the use of transcriptional inhibitors that have limitations or minimal promoters that have deficient expression levels.

Now, the inventors developed expression vectors derived from ribosomal protein 23 (RPS23) and ribosomal protein 30 (RPS30) that are transcriptionally non-inducible and constitutively active. Thus, the expression vectors are highly suitable for a number of applications, particularly for selective post-transcriptional assessment. Generally, these ribosomal protein promoters lead to weak expression levels, but, in this patent application, RPS23 and RPS30 were rendered for moderate expression. Unlike CMV and SV40 promoters, the modified RPS30IM system (wherein RPS30IM system refers to RPS30I-M1, RPS30I-M2, RPS30I-M2T, RPS30I-M1TOD as well as RPS30I-M1TOU, see below) was not activated by a number of stimuli and inducers. For example, the RPS30I-M1 system was applied to investigate responses to TNF-α or IL-α in the presence of the phosphatase inhibitor, okadaic acid, known to stabilize AU-rich elements containing-mRNAs and was found to be responsive in a manner that is independent on transcriptional induction. For more details, see herein below, and Figures and Examples.

Preferred ribosomal protein gene promoters of the invention are the promoter of ribosomal protein S23 (RPS23) and ribosomal protein S30 (RPS30), more preferably the human RPS23 promoter or human RPS30 promoter.

The sequences of RPS23 and RPS30 can be found in the RPG ribosomal protein gene database (http://ribosome.miyazaki-med.ac.jp). See also SEQ ID NOs. 1 and 2.

The gene of $Homo\ sapiens$ RPS30 or RPS23, respectively, contain several intron and exon sequence sections as well as a 5' upstream and a 3' downstream region, wherein the promoter region is in the 5' upstream region.

Furthermore preferred are sequences that can be derived from the preferred ribosomal protein gene promoters.

Furthermore, parts or partial sequences of the preferred ribosomal protein gene promoters are also preferred, such as truncated sequences of these promoters, e.g. 5' truncated sequences.

Preferably, truncated sequences that have a length of at least about 100 nucleotides are preferred, such as truncated sequences that have a length of about 100, 150, 200, 250, 300, 350, 400 nucleotides.

In other words, the truncation is of at least 50 nucleotides or about 100 nucleotides, wherein the 5' truncation is preferred. The truncation can also be of 500, 550, 600 or more nucleotides.

Thus, truncations are preferred in a range from about 100 to 1000 nucleotides including all individual integers within that range, wherein the truncation depends on the length of the wildtype or starting sequence. The term "including all individual integers within that range", when used in relation to a range, means, for example, and when e.g. the range is 100 to 500: 100, 101, 102, 103, ( . . . ) 496, 497, 498, 500.

For example, RPS30-M1 (SEQ ID NO. 3) is 5'-truncated promoter in which 600 bases were deleted from the 5'end of the wild type promoter sequence (SEQ ID NO. 1); RPS30-M2 (SEQ ID NO. 4) is 5'-truncated promoter in which 535 bases were removed from the wild type sequence of SEQ ID NO1.

The inventors have found that these preferred promoters or parts thereof can be modified for higher expression.

The modifications are mutations, deletions, substitutions of single or several nucleotides, insertion/including of nucleic acid sequences.

The following modifications are preferred:
modifying the transcriptional initiation sequence,
preferably by mutating a TATA-like sequence to the TATA signal sequence, more preferably by substituting the TATA-like signal TACAAATA with the TATA signal TATAAATA,
including at least one sp1 site-containing sequence,
preferably obtained by truncating the RPS23 promoter or the RPS30 promoter and adding at least one sp1 site-containing sequence.

In preferred embodiments, two, three, four or more sp1 site-containing sequences are included. Sp1 sites are known in the art. Examples are given herein.

For example,
RPS30-M1 (SEQ ID NO. 3), which is a 5'-truncated promoter in which 600 bases were deleted from the 5'end of the wild type promoter sequence (SEQ ID NO. 1), has two sp1 sites: TCCCGCCCCGTCCTGCG (position: 230-250 of SEQ ID NO. 3) and GGGGCGGAGC (position: 290-300 of SEQ ID NO. 3).

RPS30-M2 (SEQ ID NO. 4) is a 5'-truncated promoter in which 535 bases were removed from the wild type sequence of SEQ ID NO1. A 100 bases (position of wild type) that contain additional sp1 site was added: (position: of 4-21 of SEQ ID NO. 4 GCCGGGCA TGGTG-GCGGG) and (position: 75-87 of SEQ ID NO. 4 GGGAGGC GGAGC). In addition to the following sp1 sites: TCCCGCCCCGTCCTGCG (position: 281-297 of SEQ ID NO. 4) and GGGGCGGAGC (position: 340-49 of SEQ ID NO. 4). Thus, RPS30-M2 contains 4 sp1 sites.

For further details, see below.
The above modifications can also be combined.

The promoter region (a) furthermore preferably comprises one or several of the following
intron sequence(s) of ribosomal proteins, preferably of RPS30 and/or RPS23, or parts thereof,
preferably first intron of RPS30 (intron 1 of RPS30) or first intron of RPS23 (intron 1 of RPS23)

The intron sequences act primarily to enhance mRNA accumulation; spliced mRNAs also exhibit higher translational yields than intron-less transcripts.
exon sequence(s) of ribosomal proteins, preferably of RPS30 and/or RPS23, or parts thereof,
preferably exon 1 of RPS30 or exon 1 of RPS23
or a part of exon 2 of RPS23 for splicing, such as the first nine nucleotides of exon 2 of RPS23,
tetracycline operator (tetO) sequences, The tetracycline operator (tetO; also called tetracycline-responsive element (TRE) or tet-operator) can be located upstream or downstream of the TATA signal or TATA-like signal. The tetO sequences allow for regulation of transcription.
modified sequences wherein the modification eliminates a restriction site.
such as
a BamH1 site CACTGAG can be eliminated by mutating it into CACCTTGAG,
a ATG can be eliminated by mutating it into CTG.

For preferred combinations of the above described modifications, see below.

The expression vectors according to the present invention preferably comprise a nucleic acid sequence of any of SEQ ID NOs. 3 to 8 or a sequence complementary thereof. For further details, see below.

Reporter or Gene Sequence (b)

The reporter or gene sequence (b) is operably linked to the promoter region (a) as well as the 3'UTR (c), such that, in general, function/activity of the promoter and/or the 3'UTR can be assessed. The transcription, the mRNA level and/or the expression level of the reporter or gene serves as the signal to be measured ("read out").

Herein, the promoter is constitutively active and non-inducible (by transcriptional factors) (with minimal interference from transcriptional effects), thus leading to a transcription and expression of the gene/reporter sequence. Therefore, the expression vectors of the invention allow a selective assessment of post-transcriptional events, such as in response to cellular responses, compounds/potential drug candidates. Also, the 3'UTR and elements comprised therein can be tested with respect to their effect on post-transcription.

Any gene product can be employed as reporter or gene sequence (b) in the expression vectors. Among important gene products are reporters. A reporter that can be employed with this approach is luciferase and β-galactosidase, green and enhanced green fluorescent protein (EGFP), Renilla and firefly luciferases, other luciferases, secreted alkaline phosphatase (SEAP), chloramphenicol acetyltransferase (CAT), secreted hormone, glucose oxidase, secreted cytokine, coral reef fluorescent protein, red and yellow fluorescent proteins, and other fluorescent and bioluminescent proteins. Many companies provide reporter systems including, but not limited to, Promega, Novagen, Clontech, Invivogen, Evrogen, Clontech, Gene Systems, Genelantis, Invitrogen, etc.

In the examples disclosed herein, we used enhanced green fluorescent protein (EGFP) as an example of a reporter. When particularly coupled with advanced imaging processing, it is sensitive and has a large dynamic range. The GFP assay can be performed on living cells allowing repeated monitoring without cell lysis and other manipulations resulting in intra-well variance in fluorescence that is <6%, which does not warrant intra-well normalization of transfection (Al-Zoghaibi et al., 2007).

Different reporters are known in the art, such as, green fluorescent protein (GFP), luciferase, secreted alkaline phosphatase (SEAP), chloramphenicol acetyltransferase (CAT), secreted hormone, secreted cytokine, β-galactosidase, and other fluorescent and bioluminescent proteins. The choice of a reporter depends on the cell line used (endogenous activity), the nature of the experiment (e.g. dynamics of gene expression and transfection efficiency), and the adaptability of the assay to the chosen detection method (Naylor, 1999). Several modifications of the reporter itself have been sought to improve the reporter performance such as rapid response and magnitude of change, such as the use of destabilization elements (Zhao et al., 1995; Li et al., 1998). Green fluorescent protein (GFP) is increasingly popular because of the possibility of non-invasive monitoring of gene expression in living tissues and cells (Naylor, 1999).

The post-transcriptional activity can also be assayed using the mRNA levels. Real time RT-PCR, Northern blots, RNase protection assays, or any other mRNA or RNA detection and measurement method can be used. Alternatively, protein levels can be assayed when secreted using ELISA or other means as in the case of secreted SEAP and β-galactosidase or by Western blotting as in the case of GFP or other intracellular proteins.

Alternatively, readout and quantitation such us fluorescence and chemoluminescence from reporters, such as GFP or luciferase, respectively, can also be used.

3' Untranslated Region (3' UTR) (c)

The 3' UTR of the expression vector (c) preferably comprises or contains mRNA destabilization or stabilization elements which are derived from a 3' UTR of a cellular mRNA.

Post-transcriptional regulation can be mediated by 3' UTR that harbor mRNA destabilization elements such as AU-rich elements (for a review see Khabar and Young, 2007). Any sequence fragment of 3'UTR can be used which contains sequence elements that negatively or positively affect the post-transcriptional outcome, i.e., at mRNA or protein levels.

mRNA destabilization or stabilization elements are preferably selected from AU-rich elements, GU-rich elements, or U-rich sequences.

The expression vector(s) of the present invention comprise further elements, which are common for expression vectors and are, thus, known to the skilled artisan.

As described above, the present invention provides the use of the expression vector according to the invention for assessing post-transcriptional effects.

The expression vector(s) according to the invention are suitable for assessing post-transcriptional effects with minimal interference from transcriptional effects due to the promoter regions (a) that comprise non-inducible ribosomal protein promoters, in particular the modified ribosomal protein promoters which are modified for higher expression, as described herein.

Thus, the use of the expression vector according to the invention allows the identification of compounds that affect post-transcriptional regulation of genes/reporters.

The expression vectors according to the invention can also be used for producing an array.

Arrays, Libraries and Cell Lines of the Expression Vectors

The expression vectors of the invention are versatile means, including, but not limited to an array containing functional linear reporter/gene products in which each of the array feature contains a different post-transcriptional factor or regulatory element, obtaining a library of expression vectors, wherein each of the expression vectors contains a different post-transcriptional factor or regulatory element, obtaining cells that harbour the expression vectors of the invention that can preferably be used for assessing post-transcriptional regulation.

Arrays of the Expression Vector(s)

The present invention provides an array that can be obtained/produced according to the present invention and that comprises at least an expression reporter or gene construct of the present invention.

An "array" or "microarray" refers to is a multiplex technology used in molecular biology and in medicine. It consists of an arrayed series of several, many or even thousands of microscopic spots of molecules/probes (here: expression reporter or gene constructs), called features. Typically, the molecules/probes are attached to a solid surface by a covalent bond to a chemical matrix. The solid surface can be glass or a silicon chip. Other microarray platforms use microscopic beads, instead of the large solid support. Arrays and microarrays are known in the art.

According to the invention, a preferred array platform/format uses vessels or vessel replicates, such as in microtiter plates.

An array produced according to the present invention comprises at least an expression reporter or gene construct of the present invention, preferably at least 2 expression reporter or gene constructs, in one or more vessels, wherein each vessel contains an expression reporter or gene construct with a different 3'UTR or post-transcriptional control element(s).

Thus, each expression reporter or gene construct preferably comprises a single 3'UTR of cellular mRNA with post-transcriptional element(s), or a control 3'UTR with introduced post-transcriptional elements, whereas introduced post-transcriptional elements can be inserted by any known method of the art such as by cloning or site-directed mutagenesis.

Wherein the post-transcriptional element(s) are, for example, AU-rich elements, GU-rich elements, or U-rich elements/sequences.

Therefore, preferably each vessel or vessel replicate of the array contains an expression vector with a unique 3'UTR, i.e. the expression vector of each vessel has a different or unique 3'UTR.

A control 3'UTR can be of stable cellular mRNA, such as bovine growth hormone (BGH), rabbit beta-globin, growth hormone 3'UTR.

The arrays of the present invention can comprise further molecules/probes.

Libraries of the Expression Vector(S)

The present invention furthermore provides a library of expression vectors comprising at least two expression vectors according to the present invention, wherein each expression vector comprises a different post-transcriptional control element.

Thus, each member (=expression vector) of the library differs from the other members (=expression vectors) at least by its post-transcriptional control element(s).

Thus, each expression vector of the library preferably comprises
- a single 3'UTR of cellular mRNA with post-transcriptional element(s), or
- a control 3'UTR with introduced post-transcriptional elements, whereas introduced post-transcriptional elements can be inserted by any known method of the art such as by cloning or site-directed mutagenesis.

Wherein the post-transcriptional element(s) are, for example, AU-rich elements, GU-rich elements, or U-rich elements/sequences.

A control 3'UTR can be of stable cellular mRNA, such as bovine growth hormone (BGH), rabbit beta-globin, growth hormone 3'UTR.

Cell Lines of the Expression Vector(s)

The present invention furthermore provides a cell line that harbours the expression vector according to the present invention, and preferably expresses a reporter or gene protein therefrom.

The cell line is preferably a stable cell line.

Preferably, the expression vector comprises a single 3'UTR of cellular mRNA or a control 3'UTR with post-transcriptional elements, such as AU-rich elements, GU-rich elements, or U-rich elements. A control 3'UTR can be of stable cellular mRNA such as BGH, rabbit beta globin, growth hormone 3'UTR.

In a preferred embodiment, the single cells of the cell line differ from each other in that they harbour expression vectors that differ in their post-transcriptional control element(s).

In a preferred embodiment of the present invention, each cell line harbours an expression vector that comprises a different 3'UTR or post-transcriptional control element(s) from the expression vectors of other cell lines.

Versatility of reporter systems allows use in many applications, for example, but not limited to, drug discovery, drug target discovery, bioassay development, bioassays, cytokine bioassays, interferon response bioassays, virus response bioassays, metal response bioassays, stress response bioassay, inflammatory response bioassays, cell growth assay, cellular behavior indicator assays, angiogenesis bioassay, chemotaxis and metastasis assays, hypoxia assays, environmental changes bioassays using parameters, such as heat, nutrient, radiation, oxygen, pH, salts, toxins. Additionally, any bioassay for inhibition of above responses is also a potential application.

Method and Kit for Compound Identification

As disclosed above, the present invention furthermore provides a method for identifying compounds that affect post-transcriptional regulation, such as of reporter(s) or gene(s).

Herein, the expression vector(s), arrays, libraries of expression vectors and stable cell lines are valuable tools.

In an embodiment, linear expression cassette(s) derived from the expression vector(s) of the present invention are used. For a method of obtaining such a linear expression cassette, please see below and International patent application PCT/EP2008/005278 of Jun. 27, 2008, which is disclosed herein in its entirety by reference.

Thus, in a first step of the method,
at least one expression vector as defined herein,
at least one linear expression cassette derived from the expression vector as defined herein,
an array as defined herein,
a library of expression vectors as defined herein, and/or
a stable cell line as defined herein,
is provided.

In another step, the compound(s) to be tested are provided.

In a further step, the effect of the compound on the post-transcriptional regulation is determined.

This is achieved by detecting and determining and (optionally) quantifying the mRNA level and/or the expression level of the reporter or gene.

Thus, the method according to the present invention preferably comprises the following steps:
(1) providing
at least one expression vector as defined herein,
at least one linear expression cassette derived from the expression vector as defined herein,
an array as defined herein,
a library of expression vectors as defined herein, and/or
a stable cell line as defined herein,
(2) providing at least a compound to be tested,
(3) determining the effect of the compound on the post-transcriptional regulation by determining the mRNA level and/or the expression level of the reporter or gene.

As disclosed above, the present invention furthermore provides a kit for carrying out the method according to the present invention.

Such a kit comprises preferably
(i) at least one expression vector as defined herein,
and/or
at least one linear expression cassette derived from the expression vector as defined herein,
(ii) a transfection reagent, and
(iii) an instruction sheet.

Studies requiring post-transcriptional assessment rely on the use of transcriptional inhibitors that have limitations or minimal promoters that have deficient expression levels. Here, we develop an expression vector derived from ribosomal protein 23 (RPS23) and RPS30 that are transcriptionally non-inducible and constitutively active. Thus, it is suitable for a number of application, particularly for selective post-transcriptional assessment. Generally, these ribosomal protein promoters lead to weak expression levels, but, in this patent application, RPS23 and RPS30 were rendered for moderate expression. Unlike CMV and SV40 promoters, the modified RPS30IM was not activated by a number of stimuli and inducers.

For example, the RPSI30M system was applied to investigate responses to TNF-$\alpha$ or IL-$\alpha$ in the presence of the phosphatase inhibitor, okadaic acid, known to stabilize AU-rich elements containing-mRNAs and found responsive in a manner that is independent on transcriptional induction.

Production of the Expression Vectors of the Invention

The promoters with their introns are preferably amplified from genomic DNA using PCR with primers specific to the flanking region of each promoter/intron sequence. The primers used include the restriction sites, EcoRV and SalI sites and the resultant PCR products are cloned into an existing reporter expression vector, such as an EGFP expression vector, that was previously cut by EcoRV and SalI. Ribosomal proteins promoters can be amplified from genomic DNA of THP-1 cell line.

Other preferred methods for the production of the expression vectors of the invention is disclosed in the inventors International patent application PCT/EP2008/005278 of Jun. 27, 2008, which is disclosed herein in its entirety by reference.

These methods are also suitable for obtaining linear expression cassettes derived from the expression vectors of the present invention, such as used in the method and kit for identifying compounds that affect post-transcriptional regulation In particular, International patent application PCT/EP2008/005278 discloses a method comprising the generation of an expression active linear reporter construct which is controllable or, in other words, regulatable or tunable. This is performed by manipulating the sequence information in the forward primers which contain two regions, a 3' end region that is directed to the vector and can be "vector position-flexible", and a 5' end region that contains cis-acting inducible or repressible elements.

International patent application PCT/EP2008/005278 provides a simpler cloning-free method that utilizes PCR with a specific sequence design of the forward primer along with a universal reverse primer, which will be described in details.

Described therein is a simple cloning-free PCR-based procedure to generate gene and reporter expression cassettes that can be used in many applications in the field of life sciences. This cloning-free approach allows promoter activity assessment or transcriptional manipulations including the use of cis-acting sequences, that otherwise require cloning and time demanding manipulations, particularly in the case of introduced mutations. In particular, a cloning-free approach to generate transcriptionally controllable linear expression active DNA is described. The expression active linear DNA produced by PCR harbors a part of a promoter, a non-inducible or minimal promoter and contains full functional gene or reporter expression cassettes that include the gene or reporter cDNA and 3'UTR. Transcriptional control elements, such as cis-acting elements, or their mutant forms from several bases to 140 or 200 bases are simply appended to a common DNA sequence in a forward PCR primer that targets the upstream region of the gene or reporter gene of choice, such as reporters, by a single PCR or more, if required. With two- and three-step PCRs, one can generate a 400 bases promoter or transcriptional regulatory elements, if required. The forward 5' upstream primer is versatile in its nucleotide composition, any transcriptional element or regulatory element can be added including mutations and polymorphisms. The described regulated linear reporter gene approach, i.e. introducing a transcriptional control in the linear gene PCR product is simple, versatile and adaptable to high throughput studies that are important in both academic and pharmaceutical research and development activities including drug discovery processes. The invention can be used with any different applications in the field of life sciences including, but not limited to, drug screening, drug target screening, research tool in molecular and cell biology, personalized medicine, pharmacogenomics, and correlation of genetic variations and polymorphisms with phenotypic outcomes.

The principal advantage of the invention disclosed in International patent application PCT/EP2008/005278 is the ease of introducing a transcriptional control of gene or reporter construction, ease of sequence manipulations such as mutations and deletions, reliability, and adaptability to large scale experiments and high throughput drug screening. The assay is dependent on amplification of a functional reporter expression cassette from an optimized mammalian expression vector that is efficient when transfected as PCR product to express the protein of interest. The desired promoter sequences such as a minimal promoter with or without wild type and mutant cis-acting sequences are included in the forward primer that contains at the 5' end several nucleotides targeting a common region upstream of the gene or reporter cDNA. The sequences in the forward primer binding to a common region in the vector or source DNA can be as little as 6 nucleotides. The preferred length is more than 10 bases, particularly preferred is more than 12 bases. The source DNA which can be used for amplification can be the vector itself, a linearized vector that contains the whole functional gene product or reporter cassette, or a linear DNA generated by PCR that contains the whole functional gene product or reporter.

The inventor has used that invention with several different strategies. All of the assays employ a universal reverse primer that target the vector DNA downstream of 3' UTR and a forward primer that targets a region upstream of the reporter construct, depending on the application. In all of the strategies, each PCR is used with one forward and one universal reverse primer. The reverse primer is a universal primer that targets a region downstream of a polyA signal that is sufficient for optimal expression. The preferred distance from the polyA signal is at least 5 nucleotides, particularly preferred is more than 13 bases, and more preferred is more than 20 bases. The specific sequences in the universal primer binding to a vector or source DNA can be as little as 6 nucleotides. The preferred length is more than 10 bases, particularly preferred is more than 14 bases.

The assay is dependent on amplification of a functional gene product including a reporter expression cassette from an expression vector or DNA source that, when transfected as a linear product, is efficient to express the reporter (FIG. 1). The DNA source can be an expression vector or a fragment of the expression vector. The fragment of the expression vector should harbor the expression cassette composed of a promoter, a cDNA of the gene of interest, and a polyA signal. The vector or plasmid can be produced in abundant amounts using bacterial cultures. The fragment can be linearized by restriction fragments flanking this expression cassette. Alternatively, the expression cassette can be produced by PCR with primers flanking the expression cassette.

An optimized protocol for generating PCR products (100 µl volume) of the various embodiments is as follow: template (100-200 ng), 1×PCR buffer (1.5 mM $MgCl_2$), 200 µM dNTPs, Hot Start Taq, 2.5 U per reaction, pfx polymerase, 0.20 U per reaction, 0.5 µM final primer concentrations, and the following cycling conditions: 95° C. for 12 min and 32 cycles of: 94° C. for 30 sec, 53° C. for 30 sec, and 72° C. for 3.5 min, and final extension 72° C. for 7 min. The PCR products should be purified using, for example, Qiagen PCR purification columns.

Any gene product can be employed with the embodiments described therein. Among important gene products are reporters. A reporter that can be employed with this approach is luciferase and β-galactosidase, green and enhanced green fluorescent protein (EGFP), Renilla and firefly luciferases, other luciferases, secreted alkaline phosphatase (SEAP), chloramphenicol acetyltransferase (CAT), secreted hormone, glucose oxidase, secreted cytokine, coral reef fluorescent protein, red and yellow fluorescent proteins, and other fluorescent and bioluminescent proteins. Many companies provide reporter systems including, but not limited to, Promega, Novagen, Clontech, Invivogen, Evrogen, Clontech, Gene Systems, Genelantis, Invitrogen, etc.

In the examples disclosed therein, the inventor used enhanced green fluorescent protein (EGFP) as an example of a reporter. When particularly coupled with advanced imaging processing, it is sensitive and has a large dynamic range. The GFP assay can be performed on living cells allowing repeated monitoring without cell lysis and other manipulations resulting in intra-well variance in fluorescence that is <6%, which does not warrant intra-well normalization of transfection (Al-Zoghaibi et al., 2007). Also in some of the experiments, the inventor used the dual luciferase system using pGL plasmids that code for firefly and Renilla luciferase reporters from Promega, Inc.

The (post-)transcriptional activity due to the reporter or the gene of interest can also be assayed using the mRNA levels. Real time RT-PCR, Northern, RNase protection assay, or any other mRNA or RNA detection and measurement method can be used. Alternatively, protein levels can be assayed when secreted using ELISA or other means as in the case of secreted SEAP and β-galactosidase or by Western blotting as in the case of GFP or other intracellular proteins.

The desired promoter sequences are added to a forward primer that contains several nucleotides targeting a common region upstream of the reporter or gene cDNA and flexible 5' sequences representing the desired transcriptional factor site, its variants, or any other transcriptional control elements. Transcriptional control elements can be constitutive, inducible or repressible. A universal reverse primer that is specific to the vector DNA downstream of a stable 3' UTR is used in conjunction with the forward primer in the PCR.

We have used this approach with several different strategies; each is described herein with a demonstration of its utility with several applications.

The invention disclosed in International patent application PCT/EP2008/005278 is versatile in that it can be used to generate any minimal promoter, a portion of a promoter, an enhancer, positive or negative cis-acting sequences, inducible or repressible control elements, and 5' UTR sequences that are upstream of the gene, or a reporter. An example of a minimal promoter is the CMV minimal promoter which contains an SP1 site (reversed), CAAT (reversed), GC box, and TATA signal. Another example is the HSV-1 TK minimal promoter which contains CCAAT (inverted), SP1, GC-box, and TATA signal. The SV40 minimal promoter is another example. Moloney murine leukemia virus promoter (LASN) is another example. Strong promoters can be derived from housekeeping genes that are abundant, for example, but not limited to, eukaryotic elongation factor alpha (EEF1A1), actin gamma, actin beta, GAPDH, ribosomal proteins, etc. A list of housekeeping genes with their mRNA levels can be found in Eisenberg and Levanon (2003). Any minimal promoter can be derived from any strong promoter. For example, the following sequence tatataat may constitute a minimal promoter.

There are several embodiments that describe various variations of the PCR-based cloning-free generation of transcriptionally-controlled linear reporter constructs.

The forward primer may target a region that contains the minimal promoter. This region should be at least several nucleotides and leads to amplification of a minimal promoter. Thus, the amplification product would include the entire desired minimal promoter which itself may be as minimum as the TATA signal itself, TATAAA. Preferably, the minimal region is longer than 10 bases, more preferable is more than 15 bases, and more preferably is more than 20 bases. The position of the complementary sequences of the forward primers can be flexible allowing the researcher to choose any part of the promoter desired to be part of the resultant amplified product. This shows the tremendous flexibility and universality of the method.

Introduced sequences in the forward primer can be anywhere from several nucleotides to 140 or 150 bases since the longest possible chemically synthesized oligonucleotide that is economically attractive is 150 bases. Many companies provide oligonucleotides having a length up to 100 bases such as Sigma, Operon, and Invitrogen, and some provide up to 140 bases such as Thermo Scientific, Inc. With two- and three-step PCRs, one can generate a 400 bases promoter or transcriptional regulatory elements, if required.

The introduced sequences in the forward primer can be from a group of transcriptional factor or regulatory element sites. These sites can have a wide range of length with a minimum length of few nucleotides. Through this process they control and regulate gene expression. A notable example of cis-acting elements are, but not limited to, NF-κB elements, AP-1 elements, IFN-stimulated response elements (ISRE), metal response elements, c-myc response elements, p53 response elements, hypoxia induced factor response elements, retinoic acid response elements, glucose response elements, calcium response elements, and many others. Intracellular receptors such as hormone receptors, e.g. glucocorticoid receptor, estrogen receptor, and androgen receptor, can also mediate transcription and can reach the nucleus and bind to specific sites in the promoter, either in its native state or modified by a specific signaling event. These sequences bind a transcriptional factor and modulate gene expression. There are both positive regulatory elements such as NF-κB but also negative regulatory elements such as IFN-regulatory factor (IRF2). Examples of the forward primer sequences and examples of their utility in the PCR are disclosed in International patent application PCT/EP2008/005278.

The introduced sequences can be mutated either by a single base mutation mimicking a single nucleotide polymorphism in promoters and regulatory elements. Genetic manipulations such as deletions, insertions, and bases changes can also be part of the introduced sequences. Mutations with one or more bases can provide a control sequence for the transcriptional factor being studied. Examples are "G"→"C" substitution in the NFκB/Rel DNA binding region. The IFN-stimulated response element (ISRE), can be mutated. The introduced sequences can have progressively deleted lengths in order to map a specific regulatory element associated with a specific experimental condition. Examples are given in International patent application PCT/EP2008/005278

Multiple copies of the cis-acting enhancer element can be inserted into each construct upstream of a minimal promoter using the simple cloning-free PCR method. Despite the fact that in the examples disclosed in International patent application PCT/EP2008/005278, only two copies of NF-κB were used and one copy of ISRE was used, the response kinetics of the reporter assay can be improved through the use of more copies (Lai et al., 2006) and the use of de-stabilized forms of reporters (Li et al., 1998; Voon et al., 2005). Since the assays were performed with only one or two copies of ISRE or NF-κB, it is expected that increasing copies of these sites may result in stronger induction. In this assay, specific response elements are inserted upstream of a reporter gene. The reporter gene construct is then introduced into cells, either by transfection or electroporation. Extracellular ligands stimulate the activation of specific transcriptional factors, which will then bind to their response elements in the construct and initiate the transcription of the reporter gene or any other gene of interest. By measuring the expression of the gene including reporter genes, the activity of a specific signaling pathway under the influence of a specific drug can be monitored and quantified.

There are several embodiments disclosed in International patent application PCT/EP2008/005278 that reflect variations and the versatility of that invention in modifying the transcriptional activity in promoter studies. In one embodiment, a whole minimal promoter to be studied can be inserted using PCR in which the second part (5' end) segment of a forward primer contains introduced sequences of question to test its ability to evoke the reporter transcription and subsequently the reporter activity. In this way, any small region from the human genome or transcriptome can be used. Examples of the minimal promoters that were used as examples are disclosed in International patent application PCT/EP2008/005278. These minimal promoters can be constitutive such as, but not limited to, ribosomal protein promoters, constitutively active cellular promoters such as elongation factor promoter, actin promoters, and many others. Examples of ribosomal protein promoters are, but not limited to, RPS2 and RPL39. Examples of cellular promoters are, but not limited to, elongation factor and actin gamma promoters. Minimal promoters can also be inducible such as, but not limited to, IFNB minimal promoter which contains virus induced elements and metal response elements (FIG. 7). Examples of forward primes containing minimal promoters of constitutive and inducible elements are disclosed in International patent application PCT/EP2008/005278.

In another embodiment, negative regulatory elements such as those that bind to a transcriptional repressor that affects transcription of the reporter can be included in the forward 5' end region. A forward primer contains 3' end sequences that target a fixed region in the vector template that is upstream of a desirable promoter or promoter fragment and 5' end sequences that are flexible to accommodate desired cis-acting negative regulatory sites.

The reverse universal primer targets a region downstream of a polyA site. Purified PCR products are transfected into mammalian cells to express the reporter and to assay for its expression or activity under the desired experimental conditions. In this embodiment, it is desirable to have a strong promoter in order to achieve an acceptable sensitivity when transcription is reduced by negative regulatory elements. Examples of strong promoters are CMV promoter, SV40 promoter, (3-actin promoter, elongation factor promoter, and many others (Yew et al., 1997; Xu et al., 2001). The construct used herein has an intron. Enhancer and introns are known to enhance expression of transgenes but this may be dependent on the promoter, intron of a specific gene, and the cell line. Examples of introns are CMV intron A and rabbit β-globin introns. Expression can also be enhanced by using strong polyadenylation signals such as those derived from bovine growth hormone (BGH), rabbit β-globin gene, and SV40 polyadenylation signals.

Within the use of this embodiment, there are many negative response elements. For example, it has been shown that a negative regulatory control element is found upstream of NF-κB and can cause repression of TNF induction (Fong et al., 1994). Thus, the 5' end region in a forward primer can include a negative response element such as the TNF promoter. Other examples of negative response elements known in the field are: negative cyclic AMP (cAMP) response elements, retinoic acid response elements, negative interferon regulatory elements, negative hormone response element, NF-κB negative response elements, and many others. Some of the transcription sites that are positive regulatory transcriptional factors can act as negative response elements for other factors, such as the repressor interferon-response factor (IRF-2) overlaps with IRF-1 sites that are positive regulatory sites for interferon response (Paun and Pitha, 2007).

In another embodiment, it may be desirable to use a longer promoter sequence that is non-inducible or constitutively active and then to append the promoter in the PCR to the forward primer that contains any desired sequence or variant. FIG. 11 of International patent application PCT/EP2008/005278 shows examples of the cellular promoter and ribosomal promoters that are not activated with TNF-α, a pro-inflammatory inducer of NF-κB transcriptional factor, unlike CMV and SV40 promoters that can be activated by pro-inflammatory cytokines. In certain occasions, it may be desirable to append specific sequences to a promoter structure of more than a minimal promoter. As an example, we have constructed several vector constructs that harbor several housekeeping gene promoters, primarily ribosomal protein promoters, of which gene products are known for their increased abundance and lack of common inducible transcriptional sites such as NF-κB. We have used these to pinpoint the optimal promoter in the PCR product that gives the most sensitive detection of the EGFP reporter. The RPS23 gave the best promoter with the linear DNA product obtained by PCR using a forward primer in which its 3' end part is specific for a common vector sequence and the same universal reverse primer. As an example, the 5' end of the forward primer contains NF-κB or NF-κB non-responsive. Any regulatory transcriptional control elements can be appended in the forward 5' end part. Examples of these transcriptional control elements are given therein.

Any combination of promoter and cDNA of interest can be used with the invention disclosed in International patent application PCT/EP2008/005278. For example, SV40 minimal promoter and the luciferase reporter are used to generate a transcriptionally-controlled expression active PCR product. The forward primer can incorporate transcriptional control elements such as NF-κB and a mutant control sequence.

In another embodiment disclosed in International patent application PCT/EP2008/005278, a non-inducible promoter such as a minimal promoter or a larger non-inducible promoter can be used to construct a linear cassette with a controlled inducible reporter or any other gene product. There are many other examples of inducible elements that can be used in this strategy, i.e., controlled expression of the reporter or the gene activity. These are, but not limited to, metal response elements, heat shock response, isopropyl beta-D-thiogalactoside (IPTG), and hormone response elements such as ponasterone A induction of the EcP system and dexamethasone-MMLV promoter system (Meyer-Ficca et al., 2004). An example of hormone receptor technology is the one available from New England Biolabs by induction by a synthetic inducer, RheoSwitch Ligand RSL1, and a chimeric bipartite nuclear receptor. Other examples are the Q-mate expression system which is available from Q-biogene, in which repression of gene expression is mediated by the cumate repressor protein CymR bound to operator sites in the absence of the inducer molecule cumate. A common technology relates to is the tetracycline-responsive elements which are regulated by the repressor rtTA or the activator protein tTA, the Tet-Off and Tet-On systems, respectively (Gossen and Bujard, 2002). Doxycycline or tetracycline to turn on or off genes of interest including the reporter can be used. For example, the tetracycline-responsive positive element can be included in the 5' end of the forward primer. The resultant PCR product harboring the reporter or the gene of interest will be active or inactive (depending on whether the response element is on or off). Then, these products are transfected into cells that express either an activator or repressor, and the gene expression or activity is monitored. Another example of inducible systems is given; the disclosed approach was easily applied to generate in a cloning-free manner a PCR product expressing a gene under the control of metal responsive transcription. The metal response elements of metallothionein, MT1G and MT1G, were included in the forward primer. The PCR product was able to express the gene product EGFP reporter, when the heavy metal cadmium was used. Other metals known in the art such as zinc and copper can also be used as inducers.

The disclosed example of converting the EGFP reporter is an important embodiment of the described method of covering any expression construct harboring a gene, cDNA, peptide sequence, small inhibitory RNA sequence, or any other desired sequence into a inducible/repressible expression system. Inducible/repressible systems are important research tools particularly in the case of toxic polypeptides.

In one embodiment, the invention of International patent application PCT/EP2008/005278 can also be applied to study enhancers and 5' UTRs regulatory sequences that exist upstream of the gene. Tissue specific sequences can also be added to any of the embodiments disclosed herein. Tissue specific sequences allow the expression only in a specific tissue or cell type. For example, but not limited to, a liver specific response element can be appended to the 5' end of the forward primer to generate an expression active PCR product that is active in liver cells or hepatoma cell lines. An example of a forward primer that harbors a liver specific transcriptional site for a liver specific factor is disclosed in International patent application PCT/EP2008/005278. There are many examples of transcriptional sequence elements that are tissue-specific including, but not limited to, breast tissues, cardiac tissues, nerve tissues, gland specific tissues such as thyroid and prostate tissues, and many others.

In all above embodiments, any genetic variation can be easily swapped in the forward primer including, but not limited to, single nucleotide polymorphism, mutations of more than one nucleotide, a deletion or insertion in a specific transcriptional region, tandem arrangements of the cis-acting elements and position variations.

Stable reporter cell lines can be generated by using a vector or linear DNA cassette that contains a selectable marker. Selectable markers are, but not limited to, neomycin, blasticidin, puromycin, zeocin, hygromycin, and dihydrofolate reductase (dhfr). Because of the ease of making the reporter linear construct with the desired introduced sequences or variations, it is also expected that the generation of a stable reporter cell line is also simple. In this case, co-transfection with a plasmid or PCR product coding for the selection marker that contains the expression cassette of a selection marker is necessary.

The primary goal of the invention of International patent application PCT/EP2008/005278 was to provide a simple method for producing transcriptional control elements and transcriptional manipulations of a reporter gene as linear DNA constructs for "in vivo" applications, i.e., using assays based on living cells. Specifically, the present invention's aim is to provide a simple method for manipulating promoter and transcriptional control and regulatory elements including introduced mutations and genetic variations, without the need for the time-demanding cloning steps. The method is also useful for identifying and analyzing new cis- and trans-acting regulatory sequences/factors as well as is particularly useful for drug screening and drug discovery.

The assessment and measurement of the reporter activity can be approaches, not only of the activity of the reporter proteins, but also of the levels of the reporter proteins. Reporter levels, whether intracellular or secreted, can be measured by any detection method including Western blotting, colorimetric method, fluorescence, luminescence, biosensors, and many others. Also, mRNA levels of the reporter can be used to monitor the transcription of the promoter. The mRNA levels can be assessed and quantified by a variety of techniques including, but not limited to, semi-quantitative PCR, real-time PCR, Northern blotting, RNase protection assay, beads-dependent mRNA quantification, in situ hybridization, and others. Examples of fluorescence, luminescence, and mRNA levels are disclosed in International patent application PCT/EP2008/005278.

In general, reporters that produce a detectable signal either directly such as a fluorescent signal, a change in absorbance, and a phosphorescent signal, or indirectly by labeling with a conjugate such as a chemical substrate, antibody, or ligand can be used. A signal produced by the reporter can be detected by many methods including, but not limited to, spectroscopic, spectrophotometric, biochemical, immunochemical, electrical, photochemical, optical, thermal, pH or chemical means, visual inspection, or structural and biophysical characteristics.

Because of the ease of producing the linear reporter and introducing desired variations leading to the transcriptional control, one may expect to produce a high throughput array composed of these linear reporters harboring the different transcriptional control elements and their variations such as mutations. Nowadays, there are many high-throughput automation systems that facilitate the process including cell dispensing, transfection, and detection systems. Detection systems such as imaging of fluorescent reporters are those such as the automated imagers available from BD imaging systems (BD Dickinson, Inc.), Genetix, and Cellomics. Microplate readers and array scanners can also be applied in high throughput applications.

Thus, the method allows a versatile number of applications including, but not limited to, making a library of transcriptionally regulated functional linear reporter or gene PCR products, an array containing functional linear reporter PCR products in which each of the array feature contains a transcriptional factor or regulatory element, and a kit that contains the necessary reagents to construct the linear reporter PCR product.

Versatility of reporter systems allows use in many applications, for example, but not limited to, drug discovery, drug target discovery, bioassay development, bioassays, cytokine bioassays, interferon response bioassays, virus response bioassays, metal response bioassays, stress response bioassay, inflammatory response bioassays, cell growth assay, cellular behavior indicator assays, angiogenesis bioassay, chemotaxis and metastasis assays, hypoxia assays, environmental changes bioassays using parameters, such as heat, nutrient, radiation, oxygen, pH, salts, toxins. Additionally, any bioassay for inhibition of above responses is also a potential application.

In another embodiment disclosed in International patent application PCT/EP2008/005278, the use of non-inducible or regulatable, such as with tetracyclines, minimal promoters in post-transcriptional assessment without or with minimal interference of transcriptional assessment is disclosed therein. Specifically, the solution is given to a problem where post-transcriptional assessment is desired instead of transcriptional effects. Post-transcriptional regulation can be mediated by 3' UTR that harbor mRNA destabilization elements such as AU-rich elements (for a review see Khabar and Young, 2007). Any sequence fragment of 3'UTR can be used which contains sequence elements that negatively or positively affect the post-transcriptional outcome, i.e., at mRNA or protein levels. In the case of ribosomal protein promoters, the preferred embodiment for post-transcriptional regulation is the vectors themselves rather than the PCR product.

The various embodiments of the described technology in the entire International patent application PCT/EP2008/005278 can be applied in animals studies, such as transgenic mice or small inhibitory RNA transgenic mice.

Ribosomal Protein Promoter Sequences and Preferred Modifications

1. RPS30

The starting sequence that the inventors used for their promoter modifications can be found on the RPG ribosomal protein gene database (http://ribosome.miyazaki-med.ac.jp/rpg.cgi?mode=strc&id=HUM10033).

See also SEQ ID NO. 1.

The gene of *Homo sapiens* RPS30 contains several intron and exon sequence sections as well as a 5' upstream and a 3' downstream region. The putative transcriptional initiation box is tacaaata (underlined).

```
5' Upstream
agcgtggccttgtttgtacctccatgattgcctggctggccttgctaacctaatcacatc tgtgacgggatatagtgatgtttaatcttatgattgccttaagaattaaggcaatcagac gggttcggcggctcatgcctgtaatcccagcactttgggaggccgaggcgggcggatcac gaggtcagaagatccagtccatcctggctaacaaggtgaaacccgtctctactaaaaat acaaaaaattagccgggcatggtggcgggagcctgtagtcccagctactcgggaggctga ggcaggaggatggcgtgaatctggaggcggagcttgcagtgggccgagatcgcgccact gccctccagcctgggcgacagagcgagactccgtctcaaaaaaaaaaaaaaaaagaatta aggcaatcataattccccacgcacactcatatgctaggacccccgcccttacctgaaacg ttgtggcttatatagacactgccaggcactgtgttaagtgctcccaaagagcacccagt ctaccattttccctctcgattctatatgtacactcgggacaagttctcctgatcgaaaac ggcaaaactaaggcccaagtaggaatgccttagttttcggggttaacaatgattaacac tgagcctcacacccacgcgatgccctcagctcctcgctcagcgctctcaccaacagccgt agcccgcagcccgctggacaccggttctccatcccccgcagcgtagcccggaacatggta gctgccatctttacctgctacgccagccttctgtgcgcgcaactgtctggtcccgcccg tcctgcgcgagctgcctgcccaggcaggttcgccggtgcgagcgtaaaggggcggagcta ggactgccttgggcggtacaaatagcagggaaccgcgcggtcgctcagcagtgacgtgac acgcagcccacggtctgtactgacgcgccctcgcttcttc Exon 1
CTCTTTCTCGACTCCATCTTCGCGGTAGCTGGGACCGCCGTTCAG Intron 1
gtaagaatggggccttggctggatccgaagggcttgtagcaggttggctgcgggtcaga aggcgcgggggaaccgaagaacggggcctgctccgtggccctgctccagtccctatccg aactccttggaggcctggccttccccacgtgagccgccgcgaccaccatcccgtcgcga tcgtttctggaccgctttccactcccaaatctccttatcccagagcatttcttggcttc tcttacaagccgtcttttctttactcag Exon 2
TCGCCAATATGCAGCTCTTTGTCCGCGCCCAGGAGCTACACACCTTCGAGGTGACCGGCC

AGGAAACGGTCGCCCAGATCAAG

Intron 2
gtaaggctgcttggtgcgccctgggttccattttcttgtgctcttcactctcgcggcccg agggaacgcttacgagccttatctttccctgtag Exon 3
GCTCATGTAGCCTCACTGGAGGGCATTGCCCCGGAAGATCAAGTCGTGCTCCTGGCAGGC

GCGCCCCTGGAGGATGAGGCCACTCTGGGCCAGTGCGGGGTGGAGGCCCTGACTACCCTG

GAAGTAGCAGGCCGCATGCTTGGAG

Intron 3
gtgagtgagagaggaatgttctttgaagtaccggtaagcgtctagtgagtgtggggtgca tagtcctgacagctgagtgtcacacctatggtaatagagtacttctcactgtcttcagtt cagagtgattcttcctgtttacatccctcatgttgaacacagacgtccatgggagactga
```

-continued
```
gccagagtgtagttgtatttcagtcacatcacgagatcctagtctggttatcagcttcca cactaaaattaggtcagaccagggcccccaaagtgctctataaaattagaagctggaaga tcctgaaatgaaacttaagatttcaaggtcaaatatctgcaactttgttctcattaccta ttgggcgcagcttctctttaaaggcttgaattgagaaaagagggggttctgctgggtggca ccttcttgctcttacctgctggtgccttcctttcccactacag
```

Exon 4
```
GTAAAGTCCATGGTTCCCTGGCCCGTGCTGGAAAAGTGAGAGGTCAGACTCCTAAG
```

Intron 4
```
gtgagtgagagtattagtggtcatggtgttaggacttttttttcctttcacagctaaacca agtccctgggctcttactcggtttgccttctccctccctggagatgagcctgagggaagg gatgctaggtgtggaagacaggaaccagggcctgattaaccttcccttctccag
```

Exon 5
```
GTGGCCAAACAGGAGAAGAAGAAGAAGAAGACAGGTCGGGCTAAGCGGCGGATGCAGTAC

AACCGGCGCTTTGTCAACGTTGTGCCCACCTTTGGCAAGAAGAAGGGCCCCAATGCCAAC

TCTTAAGTCTTTTGTAATTCTGGCTTTCTCTAATAAAAAAGCCACTTAGTTCAGTC
```

3' Downstream
```
atcgcattgtttcatctttacttgcaaggcctcagggagaggtgtgcttctcgggttggt ggtatgtcccctaggagaacagtgaggcagaaaaggcagaagcctttggtatgggggggaa gaaatggtaaactacaagagaaatttcctgtgaagaaacagctacagatcctgggggggct tcagatgtaaaattggggttattccctatcctaagtaacttgatcagtcccccaggtca ttcttttcatcttctaaacagagaaggtagcaggaatcactgtggtgagaggtttgtta tggaggcagcaatagaagggatgggtgggggaagaggtttgtatagaaggtgaacctggc cgttccctgaacttggtaccagctgtggccttagagtccagggcaggaatctggtctgcc ttggttttagaagtaaatattatgttgggagcatggcctcgtttgtacctctgtgactgc ctggccggacttggtaacctaatcacatctgtgattggatatagtgaggtttcagtgttc ccaaaagttgggttacctctggggctgattcagggttctcttctggcaactgagcctccc agcacttctgaaccccacttactcattcagctaaagtttctggacctgccagttcttgag aaatagcatccaacagggtaaagcccttgggctgtggactttgactgcctgagtttggac cttctttttcttcctactccatttactgggtggctggcctttgaactaactactaattta atctctgccatctccagggctgctgtgagggttaaaggatgtaaatcaacatctggctta cagtgagtgtgtgaatcttggctattttttgtctctgtggtgttaaagacatggtttctgc cttccagcagtttagaaaggggaggatgtggacagatacaatagcatcccagagagggc ctctttttttgttttctttttctttattttattttatt
```

2. RPS23

The starting sequence that the inventors used for their promoter modifications can be found on the RPG ribosomal protein gene database (http://ribosome.miyazaki-med.acjp/rpg.cgi?mode=strc&id=HUM10025).

See also SEQ ID NO. 2.

The gene of *Homo sapiens* RPS23 contains several intron and exon sequence sections as well as a 5' upstream and a 3' downstream region.

5' Upstream
```
gtctggcacatagaaggcattttaaacatccttgctgagtgaaccaatatcccagaaac ctctcacagctagttcatcttacaggagaaacagtattaaagagttaattaaatggccag
```

-continued gcgcggtggctcacgcctgtaatcccagcacattgggaggccgaggcgggcggatcactc gaggtcaggagatcgacaccagcctggccaacatggtgaaaccccctctctactgaaaat acaaacatcagccaggcgtgatggtggaagcctgtaatcccagctactcaggaggctgag gtgggacaatcgcttgaacccgggaggcggaggttgtagtgagccaagatcgcaccactg cacaacagcctagaagacagagtgagaccctgtctcagaaaaaataaaaataaaaataa ataaatctataagtaaatgactcgccagtcaaaataaacggcaactttagggttaaaggc ccaatctggctccaaagcttggggttttagttactacactacattgcttcactatatttt acaatttactagctgcttataagtatgaattaaggctcagaagtctaattttccagacta ctcggaggactctcgccccactccactccacaaagattcagctcagcgactccttcctac tctgacctagccccgcgtcccgctctcagtggcttgggcaagagcgcctgcgcggtgagc gggtcccataaaacgcattctgggattggtagtccatgttcctccggtctccagcattca aaagaaaaaggggggaaaaaaaaccatgcaaattagatatctctgaatttcttgcaaatta aataagacgcagattctggctcaggaaagtgatgcaaacgcgtcgttttcaaaggagaga ccccagcctcgggtcaggcgcggcgcagacagcggcgcggggtccttggctgggcggggc ttgctcgcggtggcttgtggctccttcctgcggtgcttct Exon 1
CTCTTTCGCTCAGGCCCGTGGCGCCGACAGGATGG Intron 1
gtgagctgttgtggccggtttaagggcgctgcaagcgggacttggggtcttggggacggg cgggcggatgcgaatagagtagggcggggatgccatggagaggctccatggggagggc cggggaagcgccgctccaggaggcacgtggtccggcgcggaaggggcccatgaggcgtgg aggccgccgaggtcggggtaccgagggacgcagggaggccagcgcttcctcccgggcatt cgagcggggcctcgtccttcgggagaacacattctccggagccctcttcgaacgtttatt agtcggttcagggcaacttgaaggccaaatgtttggcccacaggccaataaatagtacga gagccaatcggcttaagggtttattccaggtgaggcgagtgtcttagaagatgggaaaca cgtagatggcgtgttttacggaagaactaaaatatttaattttag Exon 2
GCAAGTGTCGTGGACTTCGTACTGCTAGGAAGCTCCGTAGTCACCGACGAGACCAGAAGT

GGCATGATAAACAGTATAAGAAAGCTCATTTGGGCACAGCCCTAAAGGCCAACCCTTTTG

GAGGTGCTTCTCATGCAAAAGGAATCGTGCTGGAAAAAGT

Intron 2
gtaagtccattgctcccgtcaagttttagtttattataggaattcgagacatgaacttac gaattcttgttttgaaagtaattgcaggttttttgtgtagtagtattcatttgggcattgt ggggtaaaattgcaaagcgtttgttctatttaaaagttggtaaaattagttttttgggaat taggtagttaaggttttaatttaacgttggcctggaaggaattggagaagatactagcaa tgatgaagtaaaggacacaaacacctttactgtgggagttgttataagtaaatggcacgt gtcagctattgaactttatcgacttgataaaactaaggtgaagagaagtgacttgcatca gaattaattgaggtcatacacctaagattgagacatgaaactgccagtatttgactggtt ttgacttttaaaataataatttcatatagttctatcatatttgatggtagagccatttt aacccagacttttttttttttttttttttttttgagacagtctagctctgtcacccagg ctggtgtgcagtagcgcaagactccctgcaaccttagcctcccaggttcaagcatttctc ctgcctcagcctcccaggtagctgggattacaggcgcccactaccacaccagctaatatt

```
ttgtattttcagtagtgatggggtttcaccatgttgaccaggctagtctcaaactcctga cctcaggtgataatgcctgcttcggcctccgaaagtgctggaattacaggcgtgagccac tgtgtccggcccagactttctaattcttacctcagatacctttttcttttttctttttt ttttttgagatagggtcccttgtcacacaggctggccatcttgacgttctaggcataga tcctcccacgtcagcctcgcaagtagttgggactacaggcccacgctgccactccagtct acttttataactgtaaaaggtctagaaatttcccccattgtgctaatgaaattaagactg gcagaaaactaggttgacatcacaggacttcagctcagccatttgaggttagattgaaaa gatagaaacagtttctcattagttctctagttaatatgaaaagataatcttttcagaaa gccagctcacagtgctgtgccttttgtatttcag
```

Exon 3
```
AGGAGTTGAAGCCAAACAGCCAAATTCTGCCATTAGGAAGTGTGTAAGGGTCCAGCTGAT

CAAGAATGGCAAGAAAATCACAGCCTTTGTACCCAATGACGGTTGCTTGAACTTTATTGA

G
```

Intron 3
```
gtgagtatttcaactctatcgtaccttctgttcttggggtggcctccctcacattttat ctgatgcaagggagtttcctcacatgaaagtattttttgtgatcgccaccaacaccagaaa taaacttcttattttattccag
```

Exon 4
```
GAAAATGATGAAGTTCTGGTTGCTGGATTTGGTCGCAAAGGTCATGCTGTTGGTGATATT

CCTGGAGTCCGCTTTAAGGTTGTCAAAGTAGCCAATGTTTCTCTTTTGGCCCTATACAAA

GGCAAGAAGGAAAGACCAAGATCATAAATATTAATGGTGAAAACACTGTAGTAATAAATT

TTCATATGCC
```

3' Downstream
```
aaaaaatgtttgtatcttactgtcccctgttctcaccacgaagatcatgttcattaccac caccaccccccttatttttttatcctaaaccagcaaacgcaggacctgtaccaatttt aggagacaataagacagggttgtttcaggattctctagagttaataacatttgtaacctg gcacagtttccctcatcctgtggaataagaaaatgggatagatctggaataaatgtgcag tattgtagtattactttaagaactttaagggaacttcaaaaactcactgaaattctagtg agatactttcttttttattcttggtattttccatatcgggtgcaacacttcagttaccaa atttcattgcacatagattatcttaggtaccctggaaatgcacattcttgtatccatct tacaggggcccaagatgataaatagtaaactcaaaattgctccccactctgtttattatt taaaggtgtcaggatctgtgttgtaatgtgtctacattaatgtgtttaggagaatacagg cattggatcatttagttgatggaagtatatgccaggcaagggagataaggtatacgacaa gactgatgttttcagtatcttctcatgaggttgtcagagaccttcatgtcttcaaagact agtcagcaaatgaagtggtttagtgtagagacaagattggttgtgttttgataatttaag ctaggtattgagtacatgtggattttgctgtccacaaatacttgtttcagagttttcatg gatacagtggcatggttgaaatgaagctgtgagccttctgctttaaatctgatgtaagaa actcctgttaacaaatagtaagtatgggttaattagccctttgatcaaagcctagcttta cattgtttaggatctttggaaaacaattggtttggttgcccacttttccgtaggatcaaga gcagaacctttcacatggcacagaagaacccaggttgcgc
```

3. RPS30I-M1

SEQ ID NO. 3

```
Gatatcggcaaaactaaggccccaagtaggaatgccttagttttcggggttaacaatgatta acactcctgagcctcacacccacgcgatgccctcagctcctcgctcagcgctctcaccaaca gccgtagcccgcagccccgctggacaccgggtctccatccccgcagcgtagcccggaacatg gtagctgccatctttacctgctacgccagccttctgtgcgcgcaactgtctggtcccgcccc gtcctgcgcgagctgcctgcccaggcaggttcgccggtgcgagcgtaaaggggcggagctag gactgccttgggcggtataaatagcagggaaccgcgcggtcgctcagcagtgacgtgacacg cagcccacggtctgtactgacgcgccctcgcttcttcctctttctcgactccatcttcgcgg tagctgggaccgccgttcaggtaagaatggggccttggctgcagccgaagggcttgtagcag gttggctgcggggtcagaaggcgcggggggaaccgaagaacggggcctgctccgtggccctg ctccagtccctatccgaactccttgggaggcctggccttccccacgtgagccgccgcgacca ccatcccgtcgcgatcgtttctggaccgctttccactcccaaatctcctttatcccagagca tttcttggcttctcttacaagccgtcttttctttactcagtcgccgtcgac
```

Modifications
1. 5' truncated RPS30 promoter (+from transcriptional start site),
2. 60 bases were added that include sp1 site,
3. RPS30 exon 1,
4. first intron of RPS30, and
5. nine bases of exon 2 RPS23 for splicing.
6. The putative transcriptional initiation box was improved from tacaaata to tataaata.
7. BamH1 site CACTGAG was eliminated by mutating to CACCTTGAG.

RPS30-M1 (SEQ ID NO. 3) is a 5'-truncated promoter in which 600 bases were deleted from the 5'end of the wild type promoter sequence (SEQ ID NO. 1). RPS30-M1 has two sp1 sites: TCCCGCCCCGTCCTGCG (position 230-250) and GGGGCGGAGC (position 290-300).

4. RPS30I-M2

Modifications
1. 5' truncated RPS30 promoter (+from transcriptional start site),
2. 100 bases were added that include sp1 site,
3. RPS30 exon 1,
4. first intron of RPS30, and
5. nine bases of exon 2 RPS23 for splicing.
6. /
7. BamH1 site CACTGAG was eliminated by mutating to CACCTTGAG RPS30-M2 (SEQ ID NO. 4) is a 5'-truncated promoter in which 535 bases were removed from the wild type sequence of SEQ ID NO1. A 100 bases (position of wild type) that contain additional sp1 site was added: (position of 4-21 GCCGGGCA TGGTGGCGGG) and (position 75-87 GGGAGGC GGAGC). In addition to the following sp1 sites: TCCCGCCCCGTCCTGCG (position: 281-297) and GGGGCGGAGC (position 340-49). Thus, RPS30-M2 contains 4 sp1 sites.

SEQ ID NO. 4

```
Gatatctagccgggcatggtggcgggagcctgtagtcccagctactcggaggctgaggcag gaggatggcgtgaatctgggaggcggagcttgcagtgggccgagatcgcgccacttgagcct cacacccacgcgatgccctcagctcctcgctcagcgctctcaccaacagccgtagcccgcag ccccgctggacaccgggtctccatccccgcagcgtagcccggaacatggtagctgccatctt tacctgctacgccagccttctgtgcgcgcaactgtctggtcccgccccgtcctgcgcgagct gcctgcccaggcaggttcgccggtgcgagcgtaaaggggcggagctaggactgccttgggcg gtacaaatagcagggaaccgcgcggtcgctcagcagtgacgtgacacgcagcccacggtctg tactgacgcgccctcgcttcttcctctttctcgactccatcttcgcggtagctgggaccgcc gttcaggtaagaatggggccttggctgcagccgaagggcttgtagcaggttggctgcggggt cagaaggcgcggggggaaccgaagaacggggcctgctccgtggccctgctccagtccctatc cgaactccttgggaggcctggccttccccacgtgagccgccgcgaccaccatcccgtcgcga tcgtttctggaccgctttccactcccaaatctcctttatcccagagcatttcttggcttctc ttacaagccgtcttttctttactcagtcgccgtcgac
```

5. RPS30I-M2T

SEQ ID NO. 5

Gatatcta*gccgggcatggtggcggg*agcctgtagtcccagctactcggaggctgaggcag
gaggatggcgtgaatct*gggaggcggagc*ttgcagtgggccgagatcgcgccacttgagcct
cacacccacgcgatgccctcagctcctcgctcagcgctctcaccaacagccgtagcccgcag
ccccgctggacaccgggtctccatcccgcagcgtagcccggaacatggtagctgccatctt
tacctgctacgccagccttctgtgcgcgcaactgtctgg*tcccgccccgtcctgcg*cgagct
gcctgcccaggcaggttcgccggtgcgagcgtaaa*ggggcggagc*taggactgccttgggcg
g<u>tataaata</u>gcagggaaccgcgcggtcgctcagcagtgacgtgacacgcagcccacggtctg
tactgacgcgccctcgcttcttcctctttctgactccatcttcgcggtagctgggaccgcc
gttcaggtaagaatggggccttggctgcagccgaaggctttgtagcaggttggctgcggggt
cagaaggcgcggggggaaccgaagaacggggcctgctccgtggccctgctccagtccctatc
cgaactccttgggaggcctggccttccccacgtgagccgccgcgaccaccatcccgtcgcga
tcgtttctggaccgctttccactcccaaatctcctttatcccagagcatttcttggcttctc
ttacaagccgtcttttctttactcagtcgccgtcgac Modifications
1. 5' truncated RPS30 promoter (+from transcriptional start site),
2. 100 bases were added that include sp1 site,
3. RPS30 exon 1,
4. first intron of RPS30, and
5. nine bases of exon 2 RPS23 for splicing.
6. The putative transcriptional initiation box was improved from tacaaata to <u>tataaata</u>.
7. BamH1 site CACTGAG was eliminated by mutating to CACCTTGAG.

A 100 bases (position of wild type) that contain additional sp1 site was added: GCCGGGCA TGGTGGCGGG and GGGAGGC GGAGC. In addition to the following sp1 sites: TCCCGCCCCGTCCTGCG and GGGGCGGAGC. Thus, RPS30-M2T contains 4 sp1 sites.

6. RPS23I-M

SEQ ID NO. 6

Gatatctggccaggcgcggtggctcacgcctgtaatcccagcacattgggaggccgaggcgg
gcggatcactcccagactactcggaggactctcgccccactccactccacaaagattcagct
cagcgactccttcctactctgacctagccccgcgtcccgctctcagtggcttgggcaagagc
gcctgcgcggtgagcgggtcccataaaacgcattctgggattggtagtccatgttcctccgg
tctccagcattcaaaagaaaaaggggggaaaaaaaaaccatgcaaattagaatctctgaatttc
ttgcaaattaaataagacgcagattctggctcaggaaagtgatgcaaacgcgtcgttttcaa
aggagagaccccagcctcgggtcaggcgcggcgcagacagcggcgcggggtccttggctggg
cggggcttgctcgcggtggcttgtggctccttcctgcggtgcttctctctttcgctcaggcc
cgtggcgccgacaggctgggtgagctgttgtggccggtttaagggcgctgcaagcgggactt
ggggtcttgggacgggcgggcggatgcgaatagagtagggcggggatgccatggagaggc
tccatgggggagggccggggaagcgccgctccaggaggcacgtggtccggcgcggaaggggc
ccatgaggcgtggaggccgccgaggtcggggtaccgagggacgcagggaggccagcgcttcc
tcccgggcattcgagcggggcctcgtccttcgggagaacacattctccggagccctcttcga
acgtttattagtcggttcagggcaacttgaaggccaaatgtttggcccacaggccaataaat
agtacgagagccaatcggctaagggtttattccaggtgaggcgagtgtcttagaagatggga
aacacgtagatggcgtgttttttacggaagaactaaaatatttaattttttagGCAAGgtcgac Modifications
1. 5' truncated promoter (+392 from transcriptional start site),
2. addition of 68 bases of Sp1 site-containing sequences of RPS23 (+806 to +872 from transcription start site),
3. RPS23 exon 1,
4. first intron of RPS23, and
5. nine bases of exon 2 RPS23 for splicing.
6. /
7. The ATG site in exon 1 was mutated to CTG.

7. RPS30I-M1TOD

SEQ ID NO. 7

Gatatcggcaaaactaaggccccaagtaggaatgccttagttttcggggttaacaatgatta
acactcctgagcctcacacccacgcgatgccctcagctcctcgctcagcgctctcaccaaca
gccgtagcccgcagcccgctggacaccgggtctccatccccgcagcgtagcccggaacatg
gtagctgccatctttacctgctacgccagccttctgtgcgcgcaactgtctgg*tcccgcccc*
*gtcctgcg*cgagctgcctgcccaggcaggttcgccggtgcgagcgtaaa*ggggcggagc*tag
gactgccttgggcggtataaatagcagggaCATCCCTATCAGTGATAGACCATCCCTATCAG
TGATAGACCATCCCTATCAGTGATAGACaccgcgcggtcgctcagcagtgacgtgacacgca
gcccacggtctgtactgacgcgccctcgcttcttcctctttctcgactccatcttcgcggta
gctgggaccgccgttcaggtaagaatggggccttggctgcagccgaagggcttgtagcaggt
tggctgcggggtcagaaggcgcggggggaaccgaagaacggggcctgctccgtggccctgct
ccagtccctatccgaactccttgggaggcctggccttccccacgtgagccgccgcgaccacc
atcccgtcgcgatcgtttctggaccgctttccactcccaaatctcctttatcccagagcatt
tcttggcttctcttacaagccgtcttttctttactcagtcgccg*tcgac*

Modifications

Same as RPS30I-M1 (SEQ ID NO. 3), namely
1. 5' truncated RPS30 promoter (+from transcriptional start site),
2. 60 bases were added that include sp1 site,
3. RPS30 exon 1,
4. first intron of RPS30, and
5. nine bases of exon 2 RPS23 for splicing.
6. The putative transcriptional initiation box was improved from tacaaata to tataaata.
7. BamH1 site CACTGAG was eliminated by mutating to CACCTTGAG.

in addition 8. includes tetO sequences (bold) for regulatable of transcription downstream of the TATAAA (underlined) signal.
  RPS30-M1 has two sp1 sites: TCCCGCCCCGTCCTGCG and GGGGCGGAGC.
8. RPS30I-M1TOU Modifications Same as RPS30I-M1 (SEQ ID NO. 3), namely
1. 5' truncated RPS30 promoter (+from transcriptional start site),
2. 60 bases were added that include sp1 site,
3. RPS30 exon 1,
4. first intron of RPS30, and
5. nine bases of exon 2 RPS23 for splicing.
6. The putative transcriptional initiation box was improved from tacaaata to tataaata.
7. BamH1 site CACTGAG was eliminated by mutating to CACCTTGAG.

in addition 8. includes tetO sequences (bold) for regulatable of transcription upstream of the TATAAA (underlined) signal.

SEQ ID NO. 8

Gatatcggcaaaactaaggccccaagtaggaatgccttagttttcggggttaacaatgatta
acactcctgagcctcacacccacgcgatgccctcagctcctcgctcagcgctctcaccaaca
gccgtagcccgcagcccgctggacaccgggtctccatccccgcagcgtagcccggaacatg
gtagctgccatctttacctgctacgccagccttctgtgcgcgcaactgtctgg*tcccgcccc*
*gtcctgcg*cgagctgcctgcccaggcaggttcgccggtgcgagcgtaaagggg**CATCCCTAT
CAGTGATAGACCATCCCTATCAGTGATAGACCATCCCTATCAGTGATAGAC**cggagctagga
ctgccttgggcggtataaatagcagggaaccgcgcggtcgctcagcagtgacgtgacacgca
gcccacggtctgtactgacgcgccctcgcttcttcctctttctcgactccatcttcgcggta
gctgggaccgccgttcaggtaagaatggggccttggctgcagccgaagggcttgtagcaggt
tggctgcggggtcagaaggcgcggggggaaccgaagaacggggcctgctccgtggccctgct
ccagtccctatccgaactccttgggaggcctggccttccccacgtgagccgccgcgaccacc
atcccgtcgcgatcgtttctggaccgctttccactcccaaatctcctttatcccagagcatt
tcttggcttctcttacaagccgtcttttctttactcagtcgccg*tcgac*

The following drawings and examples illustrate the present invention without, however, limiting the same thereto.

A Ribosomal Protein Promoter Reporter constructs.

The promoters with their introns were amplified from genomic DNA using PCR with primers specific to the flanking region of each promoter/intron sequence. The primers included the restriction sites, EcoRV and SalI sites and the resultant PCR products were cloned onto EGFP expression vector that was previously cut by EcoRV and SalI. Ribosomal proteins promoters were amplified from genomic DNA of THP-1 cell line.

B HEK293 cells in 96-well plates were transfected with 150 ng of EGFP reporter vectors that are under the transcriptional control of the ribosomal protein RPS30, RPS23I-M, or RPS30I-M1 sequences. The EGFP reporter contains control stable 3'UTR. After approximately 20 hr, the cells were treated with the following compounds: okadaic acid (100 nM) or TNF-α (10 ng/ml) to induce post-transcriptional induction, if any. High resolution images were obtained automatically by BD high-content imager. Quantitation was performed with our in-house ProXcell imaging algorithm.

FIG. 2.

HEK293 cells in 96-well plates were transfected with 150 ng of EGFP reporter vectors that are under the transcriptional control of the CMV or SV40 promoter. After approximately 20 hr, the cells were treated with the following compounds: okadaic acid (100 nM) or TNF-α (10 ng/ml) to induce post-transcriptional induction, High resolution images were obtained automatically by BD high-content imager. Quantitation was performed with ProXcell imaging algorithm.

FIG. 3.

Selective for post-transcriptional regulation in the RPS30I-M linked-reporter system. HEK293 cells in 96-well plates were transfected with 150 ng of EGFP reporter vectors that are under the transcriptional control of the ribosomal protein RPS30I-M1. The EGFP reporter contains either control stable 3'UTR or 3'UTR which contain 200 bases of IL-8 3'UTR sequences known to contain mRNA destabilization elements, AU-rich elements. After approximately 20 hr, the cells were treated with the following compounds: okadaic acid (100 nM) or IL-α (3 ng/ml) to induce post-transcriptional induction, if any. High resolution images were obtained automatically by BD high-content imager. Quantitation was performed with our in-house ProXcell imaging algorithm.

FIG. 4.

Response of RPS promoter-linked reporter to ARE-3'UTR.

HEK293 cells in 96-well plates were transfected with 150 ng of EGFP reporter vectors that are under the transcriptional control of the ribosomal protein RPS30I-M1 or CMV promoter. The EGFP reporter contains either control stable 3'UTR or 3'UTR which contain 200 bases of IL-8 or TNF-α 3'UTR sequences known to contain mRNA destabilization elements, AU-rich elements. High resolution images were obtained automatically by BD high-content imager. Quantitation was performed with our in-house ProXcell imaging algorithm.

EXAMPLES

Examples of RPS-Linked Performance

Figure 1:
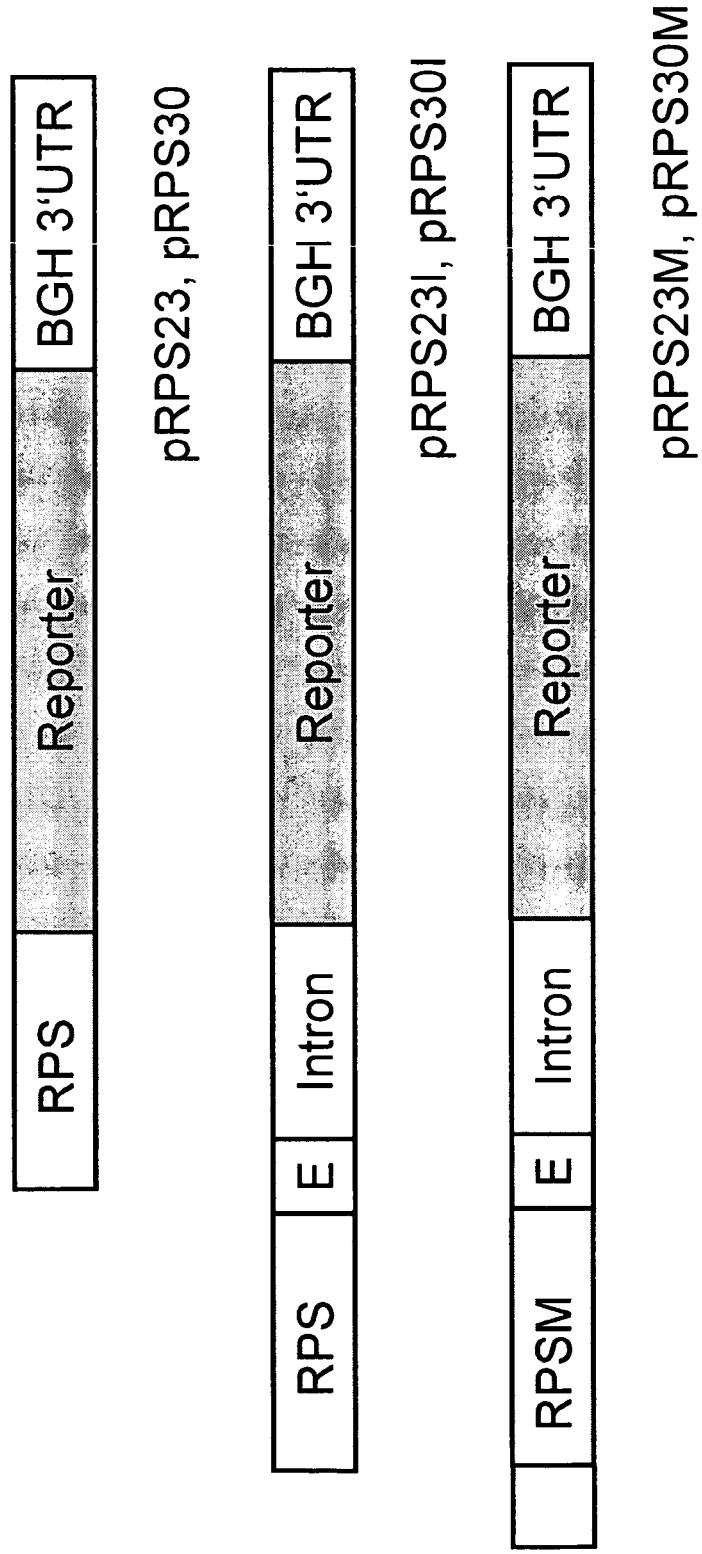
FIG. 1.
Figure 1:
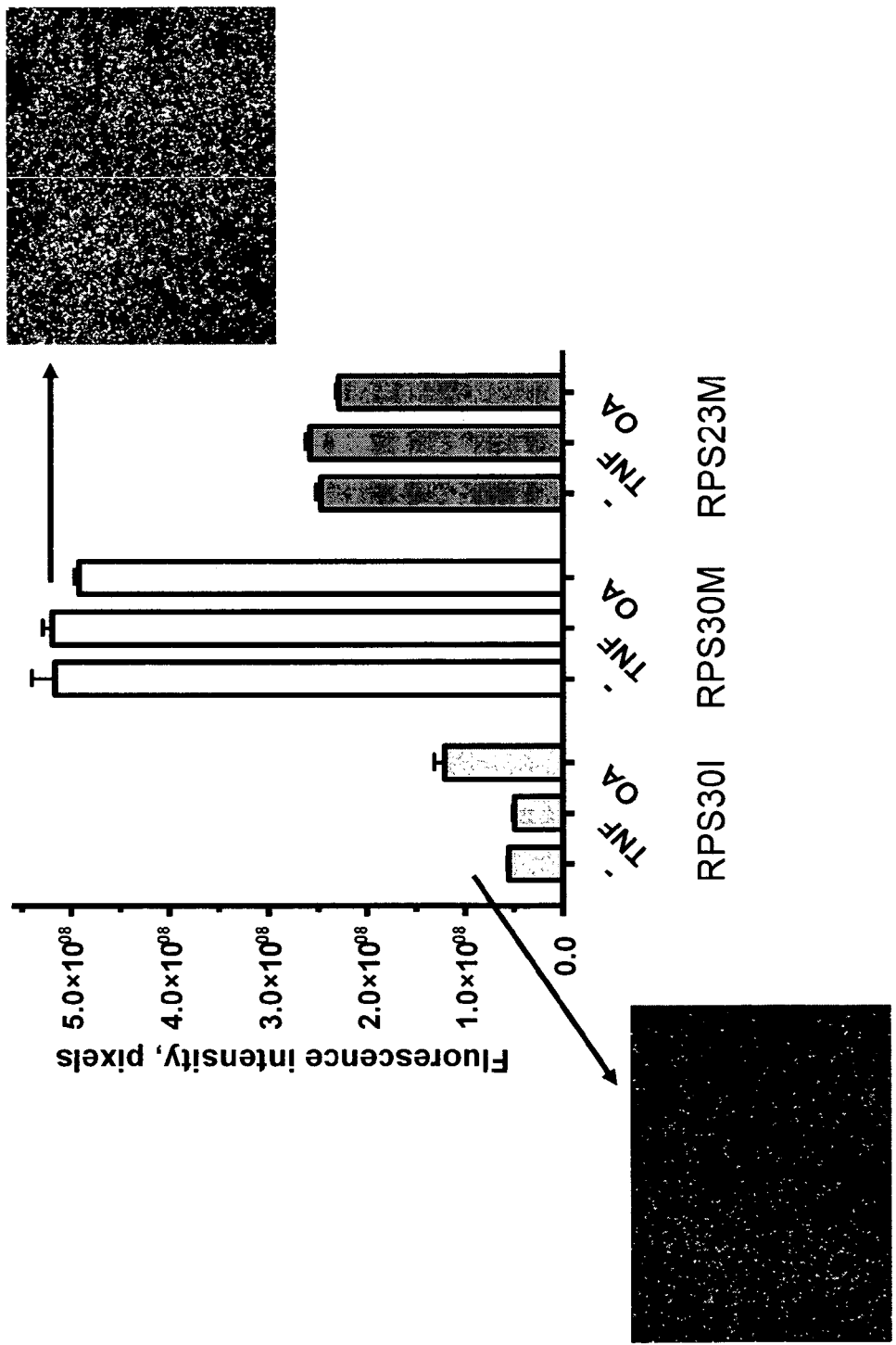
Figure 2:
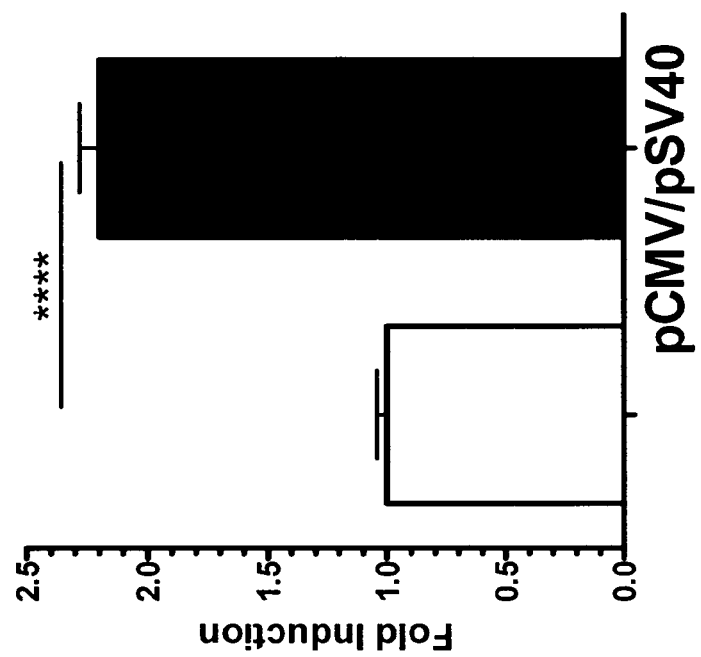

FIG. 1A shows examples of the reporter constructs utilizing ribosomal protein promoters (RPS). The modification of RPS30I-M1 and RPS23I-M resulted in significant enhancement of the vector expression when compared to the expression vector under the control of the wild type RPS30 as evaluated by the fluorescence activity due to the EGFP reporter (FIG. 1B). There was no induction by the inflammatory inducer, TNF-α, or the phosphatase inhibitor drug, okadaic acid (FIG. 1B). Unlike CMV and SV40 which tend to respond to transcriptional induction, for example, by TNF-α (FIG. 2), the RPS30I-M1 has the advantage because assessment of changes at the post-transcriptional level can be examined without interference or minimal interference from transcriptional induction.

The RPS30I-M1 promoter (FIG. 3) was chosen further for post-transcriptional assessment since it has both moderate constitutive expression and is not transcriptionally inducible by general stimulus, TNF-α or okadaic acid (FIG. 1B). The AU-rich regions, approximately 200 bases, of TNF-α and IL-8 3'UTR were cloned into the vector. Briefly, a 237 bp region (972-1209 nt: NM_000584, SEQ ID NO. 9) that belongs to the 1250 bp IL-8 3'UTR or 250 bases from TNF-α 3'UTR: (1200-1450 bp, NM_000594, SEQ ID NO. 10) were amplified by RT-PCR using specific primers that contains BamH1 and XbaI restriction sites. The PCR products were cut by BamH I and Xba I sequentially and followed by phenol extraction and ethanol precipitation. The purified cut PCR products were ligated into the EGFP expression vector that has bovine growth hormone 3'UTR that has BamH1 and XbaI sites. Recombinant colonies were verified by PCR using a forward vector specific primer and IL-8 and TNF-a 3'UTRs reverse primer. Any cloning method known in the art can be used to clone AU-rich element regions.

Figure 3:
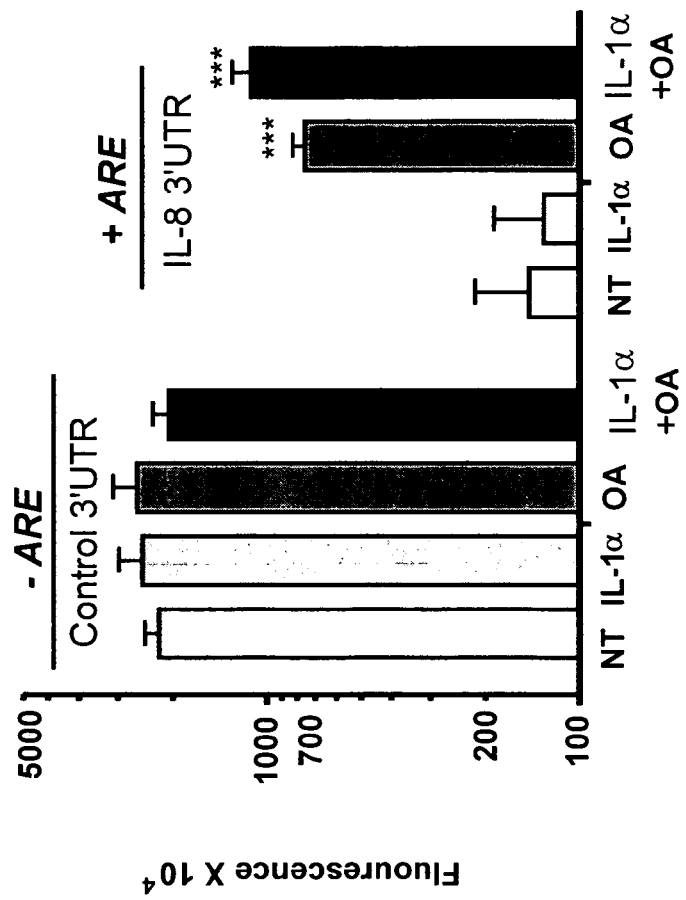

The RPS30I-M1 with control 3'UTR, RPS30I-M1 with IL-8 3'UTR, and RPS30I-M1 with TNF-α 3'UTR vectors were tested for use to assess post-transcriptional regulation. Transfected cells were stimulated with the following compounds, IL-α or okadaic acid. Any compound or modulators such as protein, expression vector, or small inhibitory RNA, or any other RNA vector can be tested for the post-transcriptional effects, i.e., induction or repression. The okadaic acid which is phosphatase inhibitor significantly increases the RPS30I-M1-IL-8 3'UTR reporter and IL-α reporters but not control RPS30-3'UTR (FIG. 3). This indicates that the use of non-inducible promoter of a ribosomal protein is useful to assess post-transcriptional effect.

Figure 4:
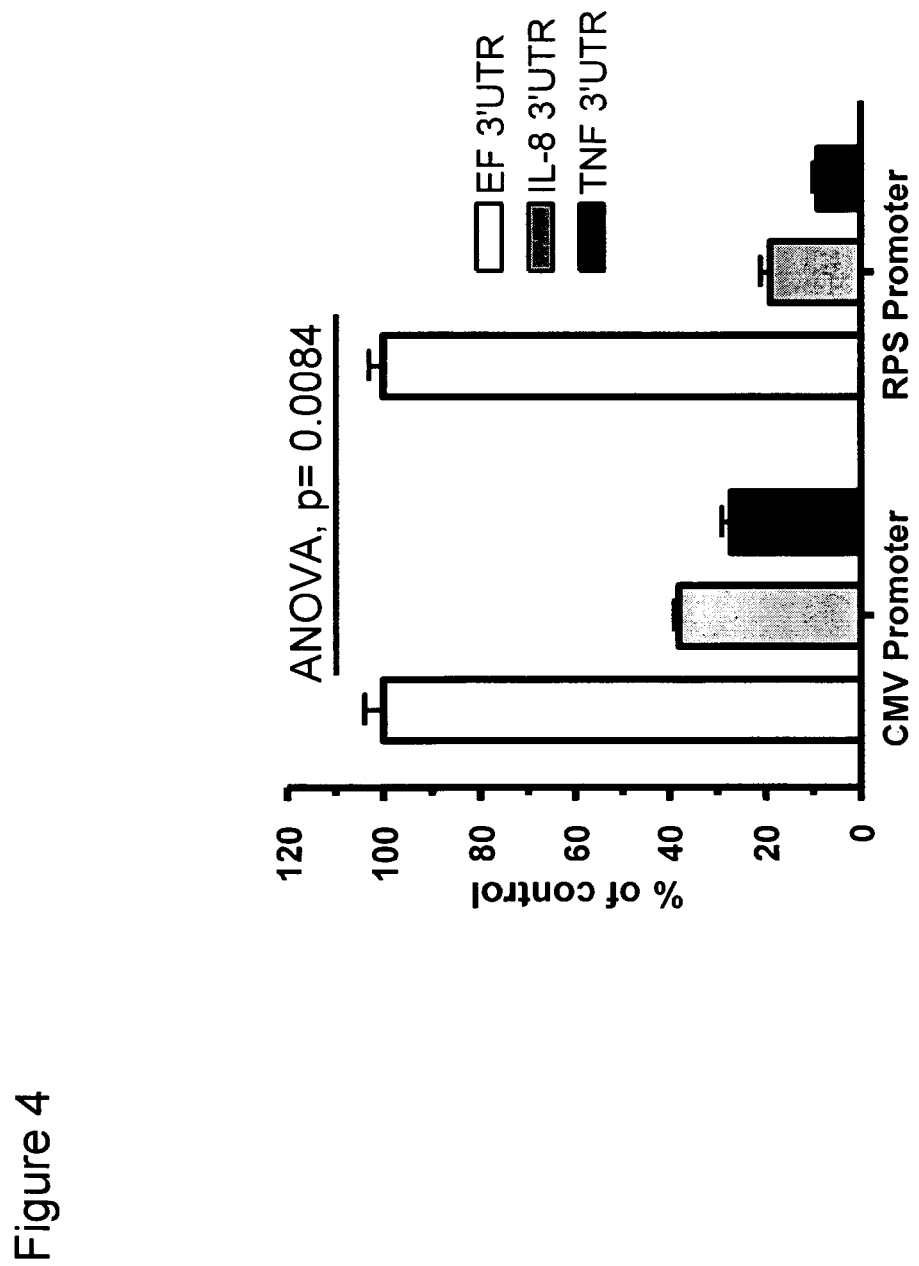

Moreover, responses to down-regulation due the presence of mRNA destabilization elements, AU-rich elements, are stronger with reporter constructs under the RPS30I-M1 promoter when compared to those with CMV promoter (FIG. 4).

The features disclosed in the foregoing description, in the claims and/or in the accompanying drawings may, both separately and in any combination thereof, be material for realizing the invention in diverse forms thereof.

REFERENCES

Al-Zoghaibi, F., Ashour, T., Al-Ahmadi, W., Abulleef, H., Demirkaya, O., and Khabar, K. S. (2007). Bioinformatics and experimental derivation of an efficient hybrid 3' untranslated region and use in expression active linear DNA with minimum poly(A) region. Gene 391, 130-139.

Calzado, M. A., Bacher, S., and Schmitz, M. L. (2007). NF-kappaB inhibitors for the treatment of inflammatory diseases and cancer. Curr Med Chem 14, 367-376.

Cooper, S. J., Trinklein, N. D., Anton, E. D., Nguyen, L., and Myers, R. M. (2006). Comprehensive analysis of transcriptional promoter structure and function in 1% of the human genome. Genome Res. 16, 1-10.

Eisenberg, E. and Levanon, E. Y. (2003). Human housekeeping genes are compact. Trends Genet 19, 362-365.

Fong, C. L., Siddiqui, A. H., and Mark, D. F. (1994). Identification and characterization of a novel repressor site in the human tumor necrosis factor alpha gene. Nucleic Acids Res 22, 1108-1114.

Gossen, M. and Bujard, H. (2002). Studying gene function in eukaryotes by conditional gene inactivation. Annu Rev Genet 36, 153-173.

Grandvaux, N., Servant, M. J., tenOever, B., Sen, G. C., Balachandran, S., Barber, G. N., Lin, R., and Hiscott, J. (2002). Transcriptional profiling of interferon regulatory factor 3 target genes: direct involvement in the regulation of interferon-stimulated genes. Journal of virology 76, 5532-5539.

Lai, C., Jiang, X., and Li, X. (2006). Development of luciferase reporter-based cell assays. Assay Drug Dev Technol 4, 307-315.

Li, X., Zhao, X., Fang, Y., Jiang, X., Duong, T., Fan, C., Huang, C. C., and Kain, S. R. (1998). Generation of destabilized green fluorescent protein as a transcription reporter. J Biol Chem 273, 34970-34975.

Khabar, K. S. and Young H. A. (2007). Post-transcriptional control of the interferon system. Biochimie 89, 761-9.

Meyer-Ficca, M. L., Meyer, R. G., Kaiser, H., Brack, A. R., Kandolf, R., and Küpper, J.-H. (2004). Comparative analysis of inducible expression systems in transient transfection studies. Anal Biochem 334 9-19.

Naylor, L. H. (1999). Reporter gene technology: the future looks bright. Biochem Pharmacol 58, 749-757.

Paun, A. and Pitha, P. M. (2007). The IRF family, revisited. Biochimie 89, 744-753.

Voon, D. C., Subrata, L. S., Baltic, S., Leu, M. P., Whiteway, J. M., Wong, A., Knight, S. A., Christiansen, F. T., and Daly, J. M. (2005). Use of mRNA- and protein-destabilizing elements to develop a highly responsive reporter system. Nucleic Acids Res 33, e27.

Xu, Z. L., Mizuguchi, H., Ishii-Watabe, A., Uchida, E., Mayumi, T., and Hayakawa, T. (2001). Optimization of transcriptional regulatory elements for constructing plasmid vectors. Gene 272, 149-156.

Yew, N. S., Wysokenski, D. M., Wang, K. X., Ziegler, R. J., Marshall, J., McNeilly, D., Cherry, M., Osburn, W., and Cheng, S. H. (1997). Optimization of plasmid vectors for high-level expression in lung epithelial cells. Hum Gene Ther 8, 575-584.

Zhao, S., Ooi, S. L., and Pardee, A. B. (1995). New primer strategy improves precision of differential display. Biotechniques 18, 842-846, 848, 850.

The invention claimed is:

1. An in vitro method for assessing a post-transcriptional effect in a cell wherein said method comprises:
   (i) providing an expression vector comprising:
      (a) a promoter region comprising a non-inducible constitutively active ribosomal protein gene promoter and at least one sp1 site-containing sequence, wherein the ribosomal protein gene promoter comprises the promoter of ribosomal protein S23 (RPS23) gene or the promoter of ribosomal protein S30 (RPS30) gene, or a fragment of said RPS23 promoter or said RPS30 promoter wherein said fragment has at least 50 nucleotides;
      (b) a reporter gene or heterologous gene; and
      (c) a 3' untranslated region (3' UTR),
      wherein said reporter gene or heterologous gene is operably linked to said promoter region and said 3' UTR;
   (ii) introducing the expression vector into a cell; and
   (iii) assaying reporter gene or heterologous gene expression in the transfected cell of step (ii) wherein expression of the reporter gene or heterologous gene is responsive to a post-transcriptional effect, and
   wherein the expression of said reporter gene or heterologous gene is independent of transcriptional induction by TNF-α or okadaic acid.

2. The method according to claim 1, wherein the post-transcriptional effect is post-transcriptional regulation of genes.

3. An in vitro method for identifying compounds that affect post-transcriptional regulation of reporter(s) or gene(s), comprising the following steps:
   1) transfecting a cell with at least one expression vector or linear expression cassette comprising:
   (a) a promoter region comprising a non-inducible constitutively active ribosomal protein gene promoter and at least one sp 1 site-containing sequence, wherein the ribosomal protein gene promoter comprises the promoter of ribosomal protein S23 (RPS23) gene or the promoter of ribosomal protein S30 (RPS30) gene, or a fragment of said RPS23 promoter or said RPS30 promoter wherein said fragment has at least 50 nucleotides; (b) a reporter gene or heterologous gene; and (c) a 3' untranslated region (3' UTR), wherein said reporter gene or heterologous gene is operably linked to said promoter region and said 3' UTR; in order to create
   a stable cell line harbouring said expression vector(s);
   2) providing at least one compound to be tested;
   3) incubating the cells created in step 1) with one or more compounds to be tested; and
   4) determining the effect of the compound(s) on the post-transcriptional regulation by determining the mRNA level and/or the expression level of the reporter gene or heterologous gene, wherein the expression of said reporter gene or heterologous gene is independent of transcriptional induction by TNF-α or okadaic acid.

4. The method according to claim 1, wherein the RPS23 promoter, the RPS30 promoter, or said fragment of the RPS23 promoter or the RPS30 promoter is modified for high expression by mutating a TATA like sequence.

5. The method according to claim 1, wherein the RPS23 promoter or the RPS30 promoter has been truncated.

6. The method according to claim 1, wherein the promoter region further comprises
   intron sequence(s) of genes encoding ribosomal proteins, exon sequence(s) of genes encoding ribosomal proteins, tetracycline operator (tetO) sequences, and/or
   modified sequences wherein the modification eliminates a restriction site.

7. The method according to claim 1, wherein the expression vector comprises the nucleic acid sequence of any of SEQ ID NOs. 3 to 8 or a sequence complementary thereto.

8. The method according to claim 1, wherein the 3' UTR comprises an mRNA destabilization or stabilization element from a 3' UTR of a cellular mRNA, wherein the mRNA destabilization or stabilization element is selected from AU-rich elements, GU-rich elements, and U-rich sequences.

9. The method according to claim 3, wherein the RPS23 promoter, the RPS30 promoter, or said fragment of the RPS23 promoter or the RPS30 promoter is modified for high expression by mutating a TATA like sequence.

10. The method according to claim 3, wherein the RPS23 promoter or the RPS30 promoter has been truncated.

11. The method according to claim 3, wherein the promoter region further comprises
   intron sequence(s) of genes encoding ribosomal proteins, exon sequence(s) of genes encoding ribosomal proteins, tetracycline operator (tetO) sequences, and/or modified sequences wherein the modification eliminates a restriction site.

12. The method according to claim 3, wherein the expression vector comprises the nucleic acid sequence of any of SEQ ID NOs. 3 to 8 or a sequence complementary thereto.

13. The method according to claim 3, wherein the 3' UTR comprises an mRNA destabilization or stabilization element from a 3' UTR of a cellular mRNA, wherein the mRNA destabilization or stabilization element is selected from AU-rich elements, GU-rich elements, and U-rich sequences.

14. An in vitro method for assessing a post-transcriptional effect in a cell wherein said method comprises:
   (i) providing an expression vector comprising:
      (a) a promoter region, wherein the promoter region consists of a non-inducible constitutively active ribosomal protein gene promoter that is from the promoter of ribosomal protein S23 (RPS23) gene or the promoter of ribosomal protein S30 (RPS30) gene, and at least one sequence selected from sp1 site-containing sequences, intron sequences of genes encoding ribosomal proteins, exon sequences of genes encoding ribosomal proteins, and tetracycline operator (tetO) sequences;
      (b) a reporter gene or heterologous gene; and
      (c) a 3' untranslated region (3' UTR),
      wherein said reporter gene or heterologous gene is operably linked to said promoter region and said 3' UTR;
   (ii) introducing the expression vector into a cell; and
   (iii) assaying reporter gene or heterologous gene expression in the transfected cell of step (ii) wherein expression of the reporter gene or heterologous gene is responsive to a post-transcriptional effect, and
   wherein the expression of said reporter gene or heterologous gene is independent of transcriptional induction by TNF-α or okadaic acid.

15. An in vitro method for identifying compounds that affect post-transcriptional regulation of reporter(s) or gene(s),
   comprising the following steps:
   1) transfecting a cell with at least one expression vector or linear expression cassette comprising:
      (a) a promoter region, wherein the promoter region consists of a non-inducible constitutively active ribosomal protein gene promoter that is from the promoter of ribosomal protein S23 (RPS23) gene or the promoter of ribosomal protein S30 (RPS30) gene, and, optionally, at least one sequence selected from sp1 site-containing sequences, intron sequences of genes encoding ribosomal proteins, exon sequences of genes encoding ribosomal proteins, and tetracycline operator (tetO) sequences; (b) a reporter gene or heterologous gene; and (c) a 3' untranslated region (3' UTR), wherein said reporter gene or heterologous gene is operably linked to said promoter region and said 3' UTR; in order to create a stable cell line harbouring said expression vector(s);
   2) providing at least one compound to be tested;
   3) incubating the cells created in step 1) with one or more compounds to be tested; and
   4) determining the effect of the compound on the post-transcriptional regulation by determining the mRNA level and/or the expression level of the reporter gene or heterologous gene, wherein the expression of said reporter gene or heterologous gene is independent of transcriptional induction by TNF-α or okadaic acid.

16. An in vitro method for assessing a post-transcriptional effect in a cell wherein said method comprises:
   (i) providing an expression vector comprising:
      (a) a promoter region comprising a non-inducible constitutively active ribosomal protein gene promoter that comprises the promoter of the human RPS23 gene that has the nucleic acid sequence of SEQ ID NO:2 or the promoter of the human RPS30 gene that has the nucleic acid sequence of SEQ ID NO:1, or a fragment of said human RPS23 promoter or said human RPS30 promoter wherein said fragment has at least 50 nucleotides;
      (b) a reporter gene or heterologous gene; and
      (c) a 3' untranslated region (3' UTR),
      wherein said reporter gene or heterologous gene is operably linked to said promoter region and said 3' UTR;
   (ii) introducing the expression vector into a cell; and
   (iii) assaying reporter gene or heterologous gene expression in the transfected cell of step (ii) wherein expression of the reporter gene or heterologous gene is responsive to a post-transcriptional effect, and
   wherein the expression of said reporter gene or heterologous gene is independent of transcriptional induction by TNF-α or okadaic acid.

17. An in vitro method for identifying compounds that affect post-transcriptional regulation of reporter(s) or gene(s),
   comprising the following steps:
   1) transfecting a cell with at least one expression vector comprising:
      (a) a promoter region comprising a non-inducible constitutively active ribosomal protein gene promoter that comprises the promoter of the human RPS23 gene that has the nucleic acid sequence of SEQ ID NO:2 or the promoter of the human RPS30 gene that has the nucleic acid sequence of SEQ ID NO:1, or a fragment of said human RPS23 promoter or said human RPS30 promoter wherein said fragment has at least 50 nucleotides; (b) a reporter gene or heterologous gene; and (c) a 3' untranslated region (3' UTR), wherein said reporter gene or heterologous gene is operably linked to said promoter region and said 3' UTR; in order to create a stable cell line harbouring said expression vector(s);
   2) providing at least one compound to be tested;
   3) incubating the cells created in step 1) with one or more compounds to be tested; and
   4) determining the effect of the compound(s) on the post-transcriptional regulation by determining the mRNA level and/or the expression level of the reporter gene or heterologous gene, wherein the expression of said reporter gene or heterologous gene is independent of transcriptional induction by TNF-α or okadaic acid.

18. The method according to claim 1, wherein the non-inducible constitutively active ribosomal protein gene promoter comprises the promoter of the human RPS23 gene that has the nucleic acid sequence of SEQ ID NO:2 or the promoter of the human RPS30 gene that has the nucleic acid sequence of SEQ ID NO:1, or a fragment of said human RPS23 promoter or said human RPS30 promoter wherein said fragment has at least 50 nucleotides.

19. The method according to claim 3, wherein the non-inducible constitutively active ribosomal protein gene promoter comprises the promoter of the human RPS23 gene that has the nucleic acid sequence of SEQ ID NO:2 or the promoter of the human RPS30 gene that has the nucleic acid sequence of SEQ ID NO:1, or a fragment of said human RPS23 promoter or said human RPS30 promoter wherein said fragment has at least 50 nucleotides.

* * * * *

UNITED STATES PATENT AND TRADEMARK OFFICE
CERTIFICATE OF CORRECTION

PATENT NO.        : 8,795,962 B2                                    Page 1 of 1
APPLICATION NO.   : 13/000556
DATED             : August 5, 2014
INVENTOR(S)       : Khalid S. Abu Khabar It is certified that error appears in the above-identified patent and that said Letters Patent is hereby corrected as shown below:

In the Specification

Column 13,
Line 41, "tatataat" should read --tatataat--.

Column 15,
Line 33, "(3-actin promoter," should read --β-actin promoter,--.

Column 21,
Line 56, "-med.acjp/" should read -- -med.ac.jp/--.

Column 27,
Line 35, "tataaata." should read --tataaata.--.

Column 32,
Line 37, "tataaata." should read --tataaata.--.

Column 36,
Line 2, "Kiipper," should read --Küpper,--.

Signed and Sealed this
Twenty-fourth Day of February, 2015

Michelle K. Lee
*Deputy Director of the United States Patent and Trademark Office*